(12) United States Patent
Nomura et al.

(10) Patent No.: US 8,232,471 B2
(45) Date of Patent: Jul. 31, 2012

(54) SQUARYLIUM DYE, METHOD OF PRODUCING THE SAME, PHOTOELECTRIC CONVERSION ELEMENT CONTAINING THE DYE, AND SOLID-STATE IMAGING DEVICE

(75) Inventors: Kimiatsu Nomura, Kanagawa (JP); Tetsu Kitamura, Kanagawa (JP); Tetsuro Mitsui, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1094 days.

(21) Appl. No.: 12/131,171

(22) Filed: Jun. 2, 2008

(65) Prior Publication Data

US 2008/0308149 A1    Dec. 18, 2008

(30) Foreign Application Priority Data

Jun. 15, 2007   (JP) .................. 2007-158568

(51) Int. Cl.
*H01L 31/0216*   (2006.01)
*H01M 4/02*   (2006.01)
(52) U.S. Cl. ........ 136/263; 136/256; 136/244; 429/111; 429/328
(58) Field of Classification Search .................. 136/263, 136/256, 244; 429/111, 328
See application file for complete search history.

(56) References Cited

U.S. PATENT DOCUMENTS

| | | | |
|---|---|---|---|
| 5,965,875 A | | 10/1999 | Merrill |
| 6,376,765 B1 | * | 4/2002 | Wariishi et al. ............... 136/263 |

FOREIGN PATENT DOCUMENTS

| | | | |
|---|---|---|---|
| JP | 63-186251 A | | 8/1988 |
| JP | 2000268892 | * | 9/2000 |
| JP | 2000285977 | * | 10/2000 |
| JP | 2003-332551 A | | 11/2003 |
| JP | 2006-106469 A | | 4/2006 |

OTHER PUBLICATIONS

Jian-Guo Chen et al., "Synthesis and Properties of Near-Infrared Absorbing Asymmetric Pyrylium-Squarylium Dyes Containing Teritiary Butyl Groups", Dyes and Pigments, 2000, pp. 93-99, vol. 46, Elsevier Science Ltd.
Seok Hwan Hwang et al., "Absorption Spectra and Electrophotographic Properties of Squarylim Dyes Containing a Nitro Group", Dyes and Pigments, 1998, pp. 359-369, vol. 39, No. 4, Elsevier Science Ltd., Great Britain.
V. Y. Merritt et al., "Organic Solar Cells of Hydroxy Squarylium", Applied Physics Letters, Oct. 1976, pp. 414-415, vol. 29, No. 7, American Institute of Physics.
Peter Peumans et al., "Small Molecular Weight Organic Thin-Film Photodetectors and Solar Cells", Journal of Applied Physics, Apr. 1, 2003, pp. 3693-3723, vol. 93, No. 7, American Institute of Physics.
Kock-Yee Law, "Organic Photoconductive Materials: Recent Trends and Developments", Chemical reviews, 1993, pp. 449-486, vol. 93, No. 1, American Chemical Society.

* cited by examiner

*Primary Examiner* — Ling Choi
(74) *Attorney, Agent, or Firm* — Sughrue Mion, PLLC

(57) ABSTRACT

A squarylium dye represented by formula (1):

Formula (1)

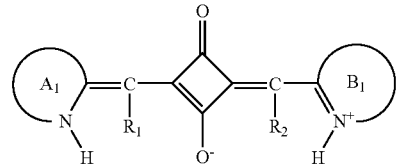

wherein $A_1$ and $B_1$ each independently represents a ring structure, and $R_1$ and $R_2$ each independently represents a substituent having a carbon number of 1 to 12.

18 Claims, 11 Drawing Sheets

COMPOUND 2

COMPOUND 3

COMPARATIVE COMPOUND 1

COMPARATIVE COMPOUND 2

SQUARYLIUM DYE, METHOD OF PRODUCING THE SAME, PHOTOELECTRIC CONVERSION ELEMENT CONTAINING THE DYE, AND SOLID-STATE IMAGING DEVICE

BACKGROUND OF THE INVENTION

1. Field of the Invention

The present invention relates to a squarylium dye having absorption in the near infrared part and a method of producing the same. The present invention also relates to a photoelectric conversion element having a photoelectric conversion part containing a pair of electrodes and an infrared organic photoelectric conversion film which contains the squarylium dye and is provided between the pair of electrodes, and a solid-state imaging device.

2. Background Art

With recent progress of organic electronics, an element using an organic dye thin film has been involved in intensive development. As one of these elements, an element using an organic material for the photoelectric conversion film is actively studied, typically including an electrophotographic device and a solar cell, and studies on various materials therefore are being made. For example, the electrophotographic material includes those described in Kock-YeeLaw, Chem. Rev., Vol. 93, p. 449 (1993), and the material for a solar cell includes those described in S. R. Forrest, J. Appl. Phys., Vol. 93, p. 3693 (2003). However, the materials described in either publication are in principle unable to favor wavelength selectivity, because the film formed has a broad absorption spectrum and the photoelectric conversion spectrum indicative of the wavelength dependency of photoelectric conversion ability becomes broad. In particular, a material suitable for the vapor deposition process that is indispensable in producing an organic electronic element, and assured of strong absorption in the near infrared region and no absorption in the visible part has been heretofore not obtained.

A squarylium dye has been intensively studied as an electrophotographic material because of its characteristic sharp absorption spectrum and good photoelectric conversion properties, but satisfactory control of the absorption spectrum is not possible. For example, a squarylium dye capable of being vapor-deposited is disclosed in Seok Hwan Hwang, et al., Dyes and Pigments, Vol. 39, p. 359 (1998), but this material has absorption in a region of short wavelength, failing in satisfactorily utilizing infrared light, and has strong absorption in the visible light region. In Jian-Guo Chen, et al., Dyes and Pigments, Vol. 46, p. 93 (2000) and JP-A-2006-106469 (the term "JP-A" as used herein means an "unexamined published Japanese patent application"), dyes having small visible absorption and having strong absorption in the near infrared region are disclosed, but their vapor deposition property is insufficient.

Conventional visible light sensors in general are produced by forming a photoelectric conversion element through formation of PN junction in a semiconductor such as Si. As for the solid-state imaging device, there is widely used a flat-type image-receiving device where photoelectric conversion elements are two-dimensionally arrayed in a semiconductor and a signal generated resulting from photoelectric conversion is read out by each photoelectric conversion element according to a CCD or CMOS format. The method for realizing a color solid-state imaging device is generally a structure where a color filter capable of transmitting only light at a specific wavelength is disposed for color separation on the light incident surface side of the above-described flat-type image-receiving device. Particularly, a single-plate sensor in which color filters capable of transmitting blue light, green light and red light are regularly disposed on respective two-dimensionally arrayed photoelectric conversion elements is well known as a system widely used at present in a digital camera and the like.

The sensor sensitive to infrared light generally uses a heat-type sensor (e.g., thermal electromotive force type, current collection effect, thermocouple effect) or a quantum-type sensor (e.g., photovoltaic effect, photoconductive effect, photoemission effect). Most of these sensors are composed of an inorganic semiconductor and since the inorganic semiconductor has broad absorption at a wavelength shorter than a certain wavelength, these sensors have a property of absorbing light in the entire region from the infrared region to the visible region.

In the case of simultaneously obtaining an image of visible light and an image of infrared light, there may be considered a method of separating the incident light into infrared light and visible light and detecting these lights by different devices, and a method of two-dimensionally disposing color filters capable of transmitting visible light and infrared light, respectively, on one device. According to such a method, an image of visible light and an image of infrared light may be obtained at the same time, but these methods have problems, for example, that: the size of the device or apparatus becomes large and the cost rises; the image is not sampled at the same point and the synthesis, processing and the like of image information are difficult; or the color filter is transparent only to light at a limited wavelength and the non-transmitted light is not utilized, giving rise to bad light utilization efficiency.

For solving these problems, a method of stacking photoelectric conversion parts capable of detecting lights at different wavelengths may be considered. As regards such a system, in so far as visible light is concerned, for example, U.S. Pat. No. 5,965,875 discloses a sensor in which a vertical stack structure is formed inside of a silicon substrate to utilize the wavelength dependency of absorption coefficient of Si and the color is separated by the difference among respective depths, and JP-A-2003-332551 discloses a sensor having a structure where an organic photoelectric conversion film is stacked on the upper side of a silicon substrate.

The system of stacking, in the vertical direction, a photoelectric conversion part for detecting infrared light and a photoelectric conversion part for detecting visible light is disadvantageous not only in that the absorption ranges of respective portions are overlapped in the depth direction of the silicone substrate to give bad spectral characteristics and the color separation is originally poor, but also in that although it is necessary in the case of using Si to further provide a photoelectric conversion part for detecting infrared light as a lowermost layer of the silicon substrate in the sensor of U.S. Pat. No. 5,965,875, infrared light is absorbed by the upper layer to reduce the infrared light reaching the lowermost layer inside of the silicon substrate and the sensitivity decreases.

As described above, when an inorganic semiconductor is used, the inorganic semiconductor alone can be hardly made to absorb only infrared light, but an organic film can be designed to absorb only light in a specific wavelength region and therefore, can be used as a layer which absorbs only infrared light.

The method of forming the organic film includes, for example, a coating method such as spin coating, and a vapor deposition method of vaporizing a material under heating in vacuum and depositing it on a base, and in view of preventing intermingling of impurities and favoring wide latitude in forming multiple layers so as to achieve high functionality, a vapor deposition method is preferred. In this case, for example, a chroconium or merocyanine-based dye representative of a dye having absorption in the infrared region has a low decomposition temperature and readily decomposes due to heating during vapor deposition and a film can be hardly formed. As for the known material having absorption in the infrared region, which can be vapor-deposited and is proved to exhibit a high photoelectric conversion function in an electrophotographic device, organic thin-film solar cell or the like, there is reported a phthalocyanine-based dye in JP-A-63-186251. However, according to the studies by the present inventors, use of a phthalocyanine-based material is disadvantageous in that a high photoelectric conversion efficiency can be hardly exerted in a wide wavelength region.

Other than these materials, a squarylium-based dye is known in Applied Physics Letters, 29, 414 (1975) as a material which can be vapor-deposited and exhibits a significant photoelectric conversion performance. The squarylium-based dye generally decomposes at the vapor deposition and therefore, it is difficult to produce an element having high performance. A system using a squarylium-based dye in a vapor-deposition system is known (Dyes and Pigments, Vol. 39, No. 4, p. 359 (1988)), but application of this system is limited to an electrophotographic system.

SUMMARY OF THE INVENTION

An object of the present invention is to provide a squarylium dye having strong absorption in the near infrared region and having only relatively small absorption in the visible region, which can be vapor-deposited without causing decomposition in the vapor deposition process and enables the production of a vapor-deposited film free of contamination, and further provide a good near infrared-absorbing organic thin film using the dye, which exhibits a large absorption intensity in the near infrared region of 700 nm or more in the thin-film absorption characteristics and exhibits only an absorption intensity of 1/10 or less of the near infrared absorption in all wavelengths of 400 to 550 nm.

Another object of the present invention is to provide a photoelectric conversion element using the squarylium-based dye, which is most suitable for a solid-state imaging device capable of simultaneously performing the photographing of a visible image based on visible light reflected from a photographic subject and the photographing of an infrared image based on infrared light.

The present invention has been accomplished by the following means.

(1) According to a first aspect of the present invention, squarylium dye represented by formula (1):

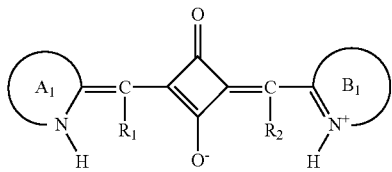

Formula (1)

wherein $A_1$ and $B_1$ each independently represents a ring structure, and $R_1$ and $R_2$ each independently represents a substituent having a carbon number of 1 to 12.

(2) The squarylium dye as described in the item (1), which is represented by formula (2):

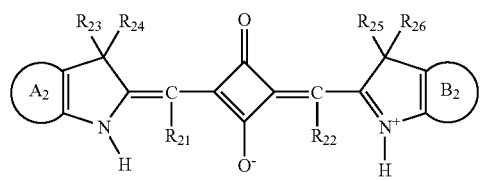

Formula (2)

wherein $R_{21}$ and $R_{22}$ each independently represents a substituent having a carbon number of 1 to 12, $R_{23}$ to $R_{26}$ each independently represents a substituent, and $A_2$ and $B_2$ each independently represents a ring structure.

(3) The squarylium dye as described in the item (1) or (2), which has a vapor deposition temperature being 30° C. or more higher than a decomposition initiating temperature.

(4) The squarylium dye as described in any one of the items (1) to (3), which has an absorption maximum wavelength of a main absorption in a thin-film absorption spectrum, and a maximum value of a relative absorbance to the main absorption at 400 to 550 nm in the thin-film absorption spectrum, wherein the absorption maximum wavelength is 700 nm or more, and the maximum value is 0.15 or less.

(5) According to a second aspect of the present invention, a method of producing a compound represented by formula (4), which comprises using a compound represented by formula (3):

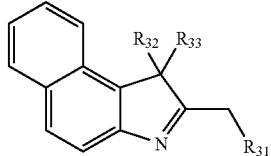

Formula (3)

wherein $R_{31}$ represents a substituent having a carbon number of 1 to 12, and $R_{32}$ and $R_{33}$ each independently represents a substituent:

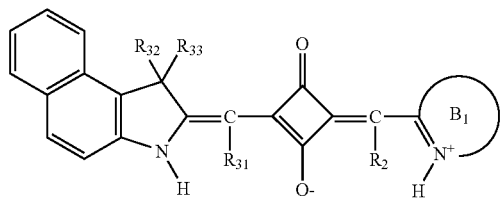

Formula (4)

wherein $R_{31}$, $R_{32}$ and $R_{33}$ have the same meanings as $R_{31}$, $R_{32}$ and $R_{33}$ in formula (3), $B_1$ represents a substituent, and $R_2$ represents a substituent having a carbon number of 1 to 12.

(6) According to a third aspect of the present invention, a photoelectric conversion element including: a photoelectric conversion part that includes a pair of electrodes and a photoelectric conversion film provided between the pair of electrodes, wherein the photoelectric conversion film comprises an organic photoelectric conversion material including a compound represented by formula (5):

Formula (5)

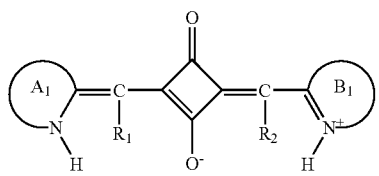

wherein $A_1$ and $B_1$ each independently represents a ring structure, and $R_1$ and $R_2$ each independently represents a substituent having a carbon number of 1 to 12.

(7) The photoelectric conversion element as described in the item (6), wherein the formula (5) is represented by formula (6):

Formula (6)

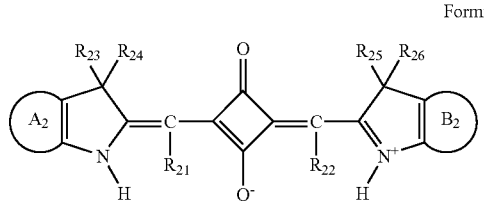

wherein $R_{21}$ and $R_{22}$ each independently represents a substituent having a carbon number of 1 to 12, $R_{23}$ to $R_{26}$ each independently represents a substituent, and $A_2$ and $B_2$ each independently represents a ring structure.

(8) The photoelectric conversion element as described in the item (6) or (7), further including: a photoelectric conversion part that includes a pair of electrodes and a photoelectric conversion film provided between the pair of electrodes, wherein the photoelectric conversion element has an absorption maximum wavelength of an absorption spectrum in a combined range of a visible region and an infrared region, the absorption maximum wavelength being 700 nm or more.

(9) The photoelectric conversion element as described in any one of the items (6) to (8), further including: a photoelectric conversion part that includes a pair of electrodes and a photoelectric conversion film provided between the pair of electrodes, wherein, in the absorption spectrum of the photoelectric conversion element in a combined range of a visible region and an infrared region, the relative value of the maximum absorbance at 400 to 650 nm with respect to the absorbance at the maximum absorption wavelength is 0.9 or less.

(10) The photoelectric conversion element as described in any one of the items (6) to (9), further including: a photoelectric conversion part that includes a pair of electrodes and a photoelectric conversion film provided between the pair of electrodes, wherein the photoelectric conversion element has sensitivity to light at 700 nm or more.

(11) The photoelectric conversion element as described in any one of the items (6) to (10), wherein the pair of electrodes comprises a transparent conducting oxide.

(12) The photoelectric conversion element as described in the item (11), wherein the transparent conducting oxide is an indium tin oxide.

(13) The photoelectric conversion element as described in any one of the items (6) to (12), further including: a semiconductor substrate on which the photoelectric conversion part is stacked; and at least one visible light photoelectric conversion part that is provided between the semiconductor substrate and the photoelectric conversion part, has an absorption maximum in the visible region of the absorption spectrum in the combined range of a visible region and an infrared region, and generates an electric charge according to light absorbed.

(14) The photoelectric conversion element as described in the item (13), wherein the semiconductor substrate includes: an accumulation part that accumulates an electric charge generated in each of the photoelectric conversion part and the visible light photoelectric conversion part; and a signal read-out part that reads out a signal according to the electric charge accumulated in the accumulation part.

(15) The photoelectric conversion element as described in any one of the items (6) to (12), further including: a semiconductor substrate on which the photoelectric conversion part is stacked; and at least one visible light photoelectric conversion part that is provided inside of the semiconductor substrate, has an absorption peak in the visible region of the absorption spectrum in the combined range of a visible region and an infrared region, and generates an electric charge according to light absorbed.

(16) The photoelectric conversion element as described in the item (15), wherein the semiconductor substrate includes: an accumulation part that accumulates an electric charge generated in the photoelectric conversion part; and a signal read-out part that reads out a signal according to the electric charge accumulated in the accumulation part.

(17) The photoelectric conversion element as described in any one of the item (13) to (16), wherein the at least one visible light photoelectric conversion part comprises a plurality of visible light photoelectric conversion parts, an the visible light photoelectric conversion parts have an absorption peak at wavelengths different from each other.

(18) The photoelectric conversion element as claimed in claim 17, wherein the visible light photoelectric conversion parts are stacked in the direction in which light is incident on the photoelectric conversion part.

(19) The photoelectric conversion element as described in the item (17), wherein the visible light photoelectric conversion parts are arrayed in the direction vertical to the direction in which light is incident on the photoelectric conversion part.

(20) The photoelectric conversion element as described in the item (17), wherein the visible light photoelectric conversion parts include three visible light photoelectric conversion parts, and the three visible light photoelectric conversion parts include an R photoelectric conversion part that absorbs light in the red wavelength region, a G photoelectric conversion part that absorbs light in the green wavelength region, and a B photoelectric conversion part that absorbs light in the blue wavelength region.

(21) The photoelectric conversion element as claimed in any one of the items (13) to (20), wherein the photoelectric conversion part and the at least one visible light photoelectric conversion part are overlapped as viewed in plane such that light transmitted through the photoelectric conversion part enters the at least one visible light photoelectric conversion part.

(22) The photoelectric conversion element as described in any one of the items (6) to (21), wherein the photoelectric conversion film includes at least one of a hole blocking layer and an electron blocking layer.

(23) According to a fourth aspect of the present invention, a solid-state imaging device includes: a photoelectric conversion element according to any one of the items (6) to (22), wherein at least one photoelectric conversion part is disposed on the same plane in an array manner.

According to the present invention, a squarylium-based dye having an absorption maximum value in the infrared region with a small visible light absorbance and exhibiting high photoelectric conversion efficiency for infrared light, and a photoelectric conversion element containing the dye can be provided. Also, a photoelectric conversion element most suitable for a solid-state imaging device capable of simultaneously performing the photographing of a visible image based on visible light reflected from a photographic subject structure and the photographing of an infrared image based on infrared light can be provided.

According to the production process of a compound represented by formula (4), comprising using a compound of formula (3), of the present invention, the difference between the vapor deposition temperature and the decomposition initiating temperature is large, so that a squarylium dye capable of being vapor-deposited without containing impurities and assured of a strong absorption intensity in the near infrared region with small absorption in the visible part can be obtained. Furthermore, when vapor deposition is performed using the dye of the present invention, a dye film assured of large absorption intensity with small absorption in the visible part and reduced in the impurities ascribable to the decomposition product of the dye can be obtained.

BRIEF DESCRIPTION OF THE DRAWINGS

The invention disclosed herein will be understood better with reference to the following drawings of which.

DETAILED DESCRIPTION OF THE INVENTION

Figure 1:
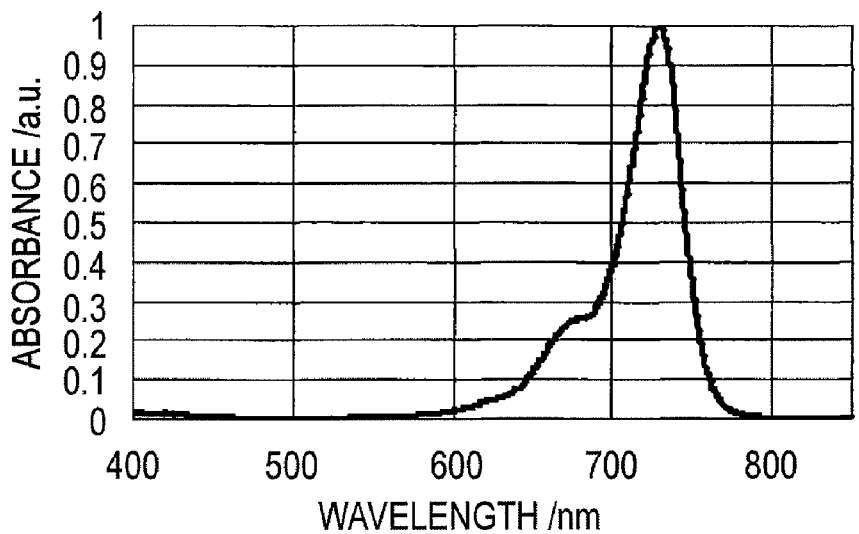
FIG. 1 is solution absorption spectrum of Compound 1.
Figure 2:
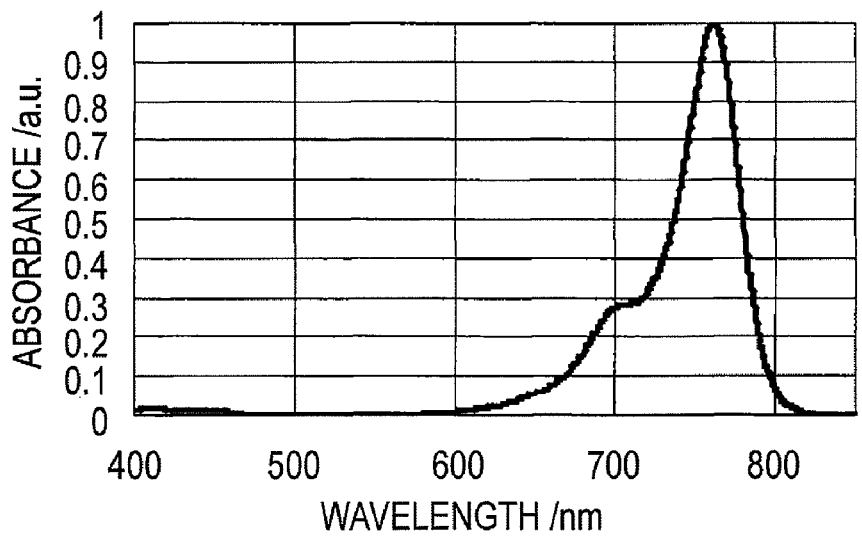
FIG. 2 is solution absorption spectrum of Compound 2.
Figure 3:
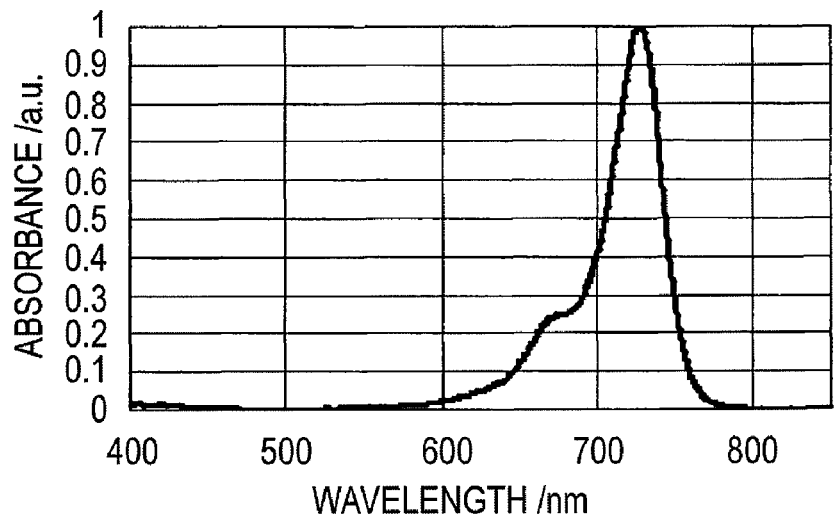
FIG. 3 is a solution absorption spectrum of Compound 3.
Figure 4:
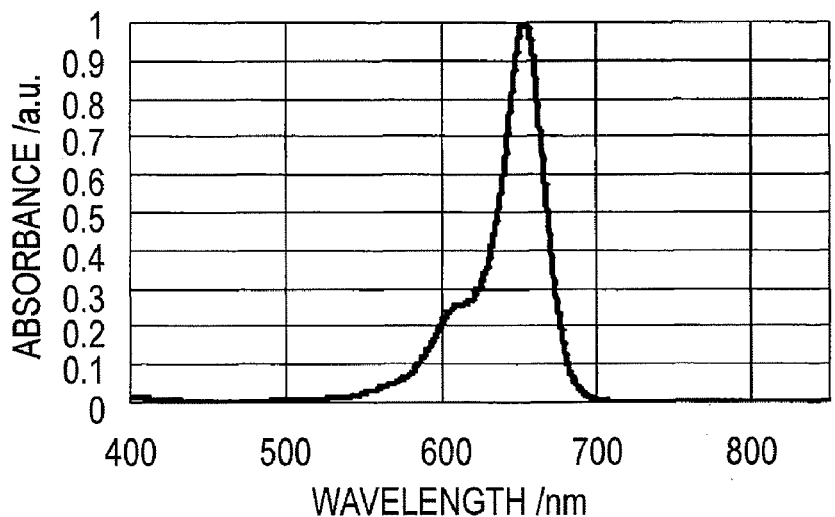
FIG. 4 is a solution absorption spectrum of Comparative Compound 1.
Figure 5:
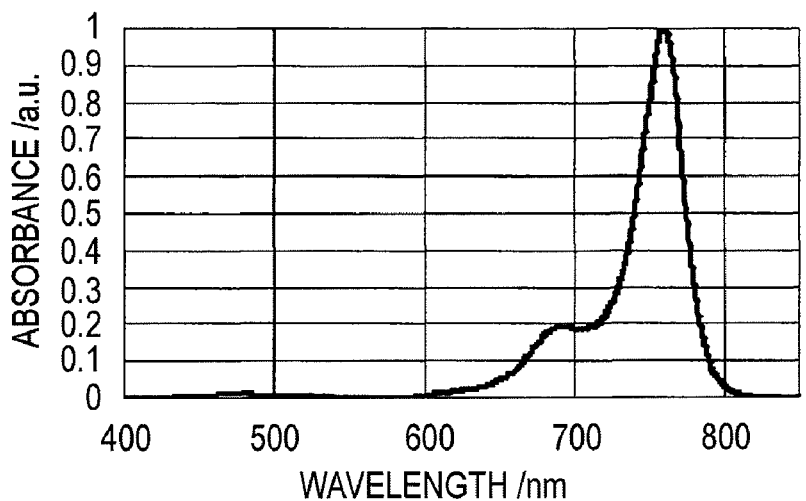
FIG. 5 is a solution absorption spectrum of Comparative Compound 2.
Figure 6:
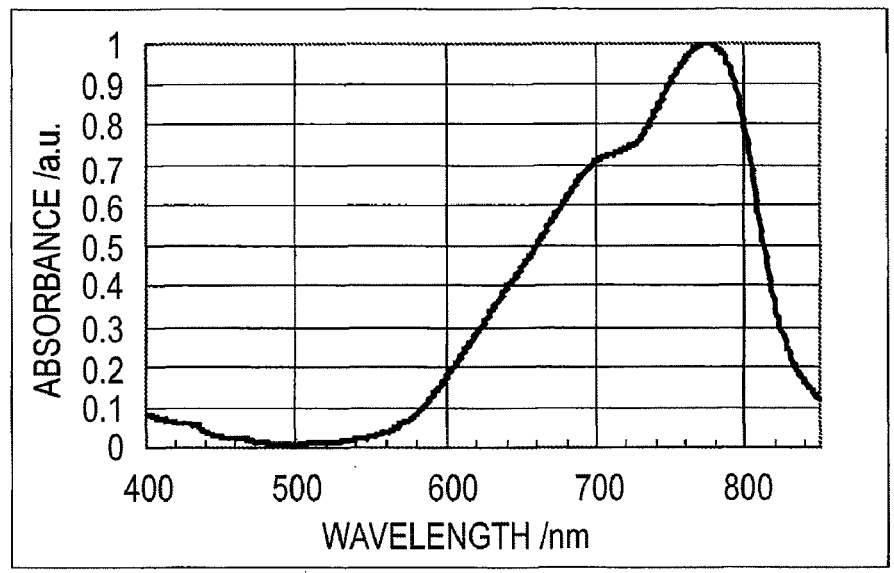
FIG. 6 is a film absorption spectrum of Compound 1.
Figure 7:
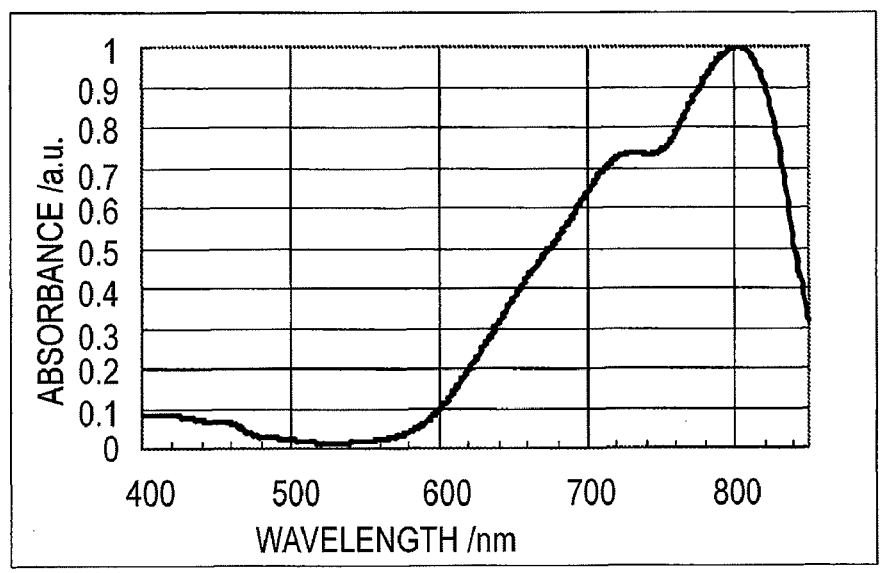
FIG. 7 is a film absorption spectrum of Compound 2.
Figure 8:
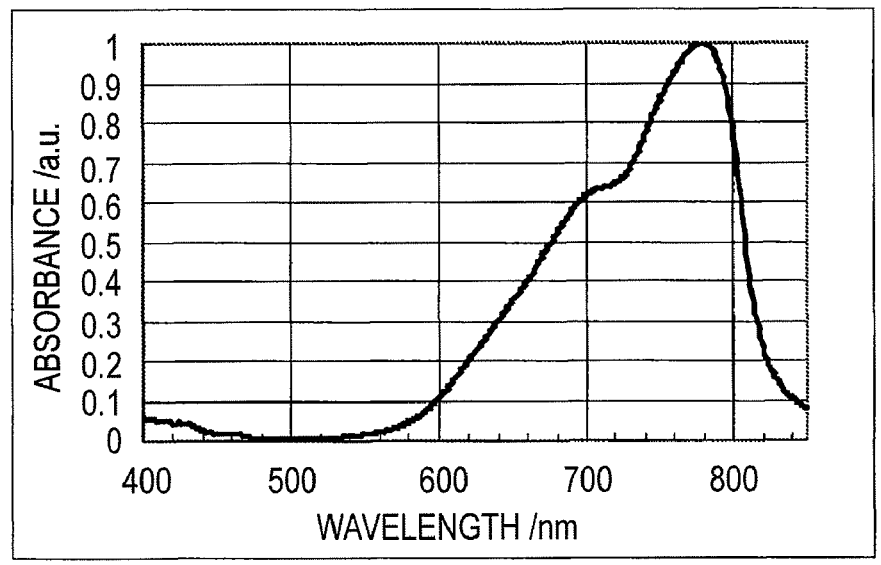
FIG. 8 is a film absorption spectrum of Compound 3.
Figure 9:
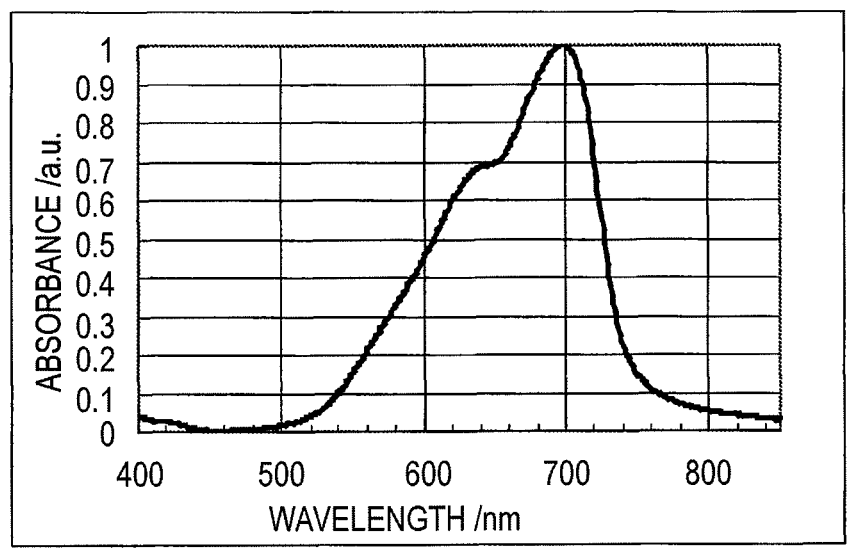
FIG. 9 is film absorption spectrum of Comparative Compound 1.
Figure 10:
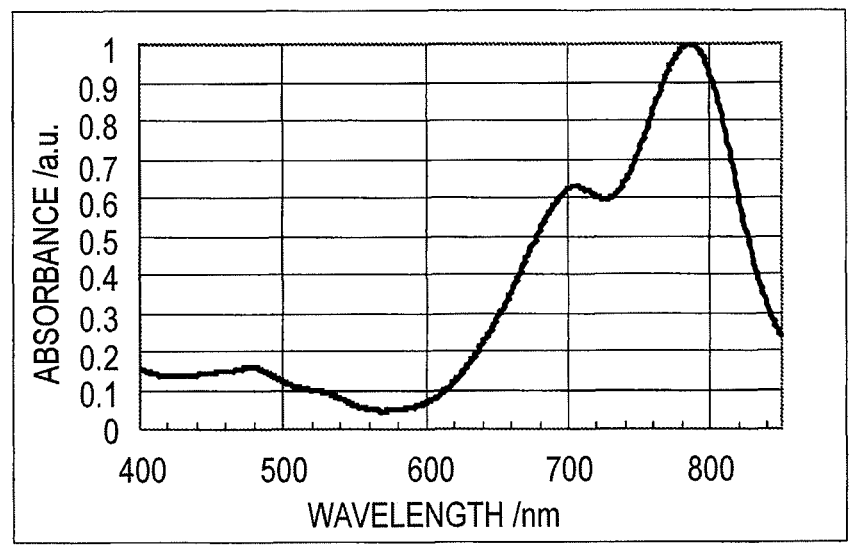
FIG. 10 is a film absorption spectrum of Comparative Compound 2.

The squarylium dye of the present invention is described in detail below.

The dye compound represented by formulae (1) and (5) is described. $A_1$ and $B_1$ each independently represents a ring structure. The ring $A_1$ is denoted as an enamine structure and the ring $B_1$ is denoted as an iminium structure, but these structures may replace each other by tautomerism. In the following, a ring $A_1$ taking an enamine structure and a ring $B_1$ taking an enamine structure are described but needless to say, these rings each includes a ring taking an iminium structure produced by tautomerism.

$A_1$ and $B_1$ each is preferably a pyrrole ring, an oxazole ring, a thiazole ring, an imidazole ring, a pyridine ring, a pyrimidine ring or a pyridazine ring, more preferably a pyrrole ring, an oxazole ring, a thiazole ring or a pyridine ring. This ring structure may be deprived of aromaticity, like a [3H]-pyrrole ring. In addition to the above-described ring structure, the ring structure is preferably a benzo-condensed ring and is preferably an indole ring, a benzoxazole ring, a benzothiazole ring, a benzimidazole ring, a quinoline ring, a benzopyrimidine ring or a benzopyridazine ring, more preferably an indole ring, a benzoxazole ring, a benzothiazole ring or a quinoline ring. These ring structures each may further have a substituent W. Examples of the substituent W include the followings.

The substituent W may be any substituent and is not particularly limited, but examples thereof include a halogen atom, an alkyl group (including a cycloalkyl group, a bicycloalkyl group and a tricycloalkyl group), an alkenyl group (including a cycloalkenyl group and a bicycloalkenyl group), an alkynyl group, an aryl group, a heterocyclic group (may also be referred to as a hetero ring group), a cyano group, a hydroxyl group, a nitro group, a carboxyl group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group (including an anilino group), an ammonio group, an acylamino group, an aminocarbonylamino group, an alkoxycarbonylamino group, an aryloxycarbonylamino group, a sulfamoylamino group, an alkyl- or aryl-sulfonylamino group, a mercapto group, an alkylthio group, an arylthio group, a heterocyclic thio group, a sulfamoyl group, a sulfo group, an alkyl- or aryl-sulfinyl group, an alkyl- or aryl-sulfonyl group, an acyl group, an aryloxycarbonyl group, an alkoxycarbonyl group, a carbamoyl group, an aryl or heterocyclic azo group, an imido group, a phosphino group, a phosphinyl group, a phosphinyloxy group, a phosphinylamino group, a phosphono group, a silyl group, a hydrazino group, a borate group ($-B(OH)_2$), a phosphate group ($-OPO(OH)_2$), a sulfato group ($-OSO_3H$) and other known substituents.

More particularly, W represents, for example, the following (1) to (48):
(1) a halogen atom,
   e.g., fluorine, chlorine, bromine, iodine,
(2) an alkyl group,
   a linear, branched or cyclic, substituted or unsubstituted alkyl group; the alkyl group includes, for example, (2-a) to (2-e):
(2-a) an alkyl group,
   preferably an alkyl group having a carbon number of 1 to 30 (e.g., methyl, ethyl, n-propyl, isopropyl, tert-butyl, n-octyl, eicosyl, 2-chloroethyl, 2-cyanoethyl, 2-ethylhexyl),
(2-b) a cycloalkyl group,
   preferably a substituted or unsubstituted cycloalkyl group having a carbon number of 3 to 30 (e.g., cyclohexyl, cyclopentyl, 4-n-dodecylcyclohexyl),
(2-c) a bicycloalkyl group, preferably a substituted or unsubstituted bicycloalkyl group having a carbon number of 5 to 30 (e.g., bicyclo[1,2,2]heptan-2-yl, bicyclo[2,2,2]octan-3-yl),
(2-d) a tricycloalkyl group,
preferably a substituted or unsubstituted tricycloalkyl group having a carbon number of 7 to 30 (e.g., 1-adamantyl), and
(2-e) a polycyclic cycloalkyl group having many ring structures,
here, the alkyl group in the substituent described below (for example, an alkyl group in an alkylthio group) means an alkyl group having such a concept but also includes an alkenyl group and an alkynyl group,
(3) an alkenyl group,
a linear, branched or cyclic, substituted or unsubstituted alkenyl group; the alkenyl group includes (3-a) to (3-c):
(3-a) an alkenyl group,
preferably a substituted or unsubstituted alkenyl group having a carbon number of 2 to 30 (e.g., vinyl, allyl, prenyl, geranyl, oleyl),
(3-b) a cycloalkenyl group,
preferably a substituted or unsubstituted cycloalkenyl group having a carbon number of 3 to 30 (e.g., 2-cyclopenten-1-yl, 2-cyclohexen-1-yl),
(3-c) a bicycloalkenyl group,
a substituted or unsubstituted bicycloalkenyl group, preferably a substituted or unsubstituted bicycloalkenyl group having a carbon number of 5 to 30 (e.g., bicyclo[2,2,1]hept-2-en-1-yl, bicyclo[2,2,2]oct-2-en-4-yl)],
(4) an alkynyl group,
preferably a substituted or unsubstituted alkynyl group having a carbon number of 2 to 30 (e.g., ethynyl, propargyl, trimethylsilylethynyl),
(5) an aryl group,
preferably a substituted or unsubstituted aryl group having a carbon number of 6 to 30 (e.g., phenyl, p-tolyl, naphthyl, m-chlorophenyl, o-hexadecanoylaminophenyl, ferrocenyl),
(6) a heterocyclic group,
preferably a monovalent group obtained by removing one hydrogen atom from a 5- or 6-membered substituted or unsubstituted, aromatic or non-aromatic heterocyclic compound, more preferably a 5- or 6-membered aromatic heterocyclic group having a carbon number of 3 to 50 (e.g., 2-furyl, 2-thienyl, 2-pyrimidinyl, 2-benzothiazolyl; the heterocyclic group may also be a cationic heterocyclic group such as 1-methyl-2-pyridinio and 1-methyl-2-quinolinio),
(7) a cyano group, (8) a hydroxyl group, (9) a nitro group, (10) a carboxyl group,
(11) an alkoxy group,
preferably a substituted or unsubstituted alkoxy group having a carbon number of 1 to 30 (e.g., methoxy, ethoxy, isopropoxy, tert-butoxy, n-octyloxy, 2-methoxyethoxy),
(12) an aryloxy group,
preferably a substituted or unsubstituted aryloxy group having a carbon number of 6 to 30 (e.g., phenoxy, 2-methylphenoxy, 4-tert-butylphenoxy, 3-nitrophenoxy, 2-tetradecanoylaminophenoxy),
(13) a silyloxy group,
preferably a silyloxy group having a carbon number of 3 to 20 (e.g., trimethylsilyloxy, tert-butyldimethylsilyloxy),
(14) a heterocyclic oxy group,
preferably a substituted or unsubstituted heterocyclic oxy group having a carbon number of 2 to 30 (e.g., 1-phenyltetrazol-5-oxy, 2-tetrahydropyranyloxy),
(15) an acyloxy group,
preferably a formyloxy group, a substituted or unsubstituted alkylcarbonyloxy group having a carbon number of 2 to 30, or a substituted or unsubstituted arylcarbonyloxy group having a carbon number of 6 to 30 (e.g., formyloxy, acetyloxy, pivaloyloxy, stearoyloxy, benzoyloxy, p-methoxyphenylcarbonyloxy),
(16) a carbamoyloxy group,
preferably a substituted or unsubstituted carbamoyloxy group having a carbon number of 1 to 30 (e.g., N,N-dimethylcarbamoyloxy, N,N-diethylcarbamoyloxy, morpholinocarbonyloxy, N,N-di-n-octylaminocarbonyloxy, N-n-octylcarbamoyloxy),
(17) an alkoxycarbonyloxy group,
preferably a substituted or unsubstituted alkoxycarbonyloxy group having a carbon number of 2 to 30 (e.g., methoxycarbonyloxy, ethoxycarbonyloxy, tert-butoxycarbonyloxy, n-octylcarbonyloxy),
(18) an aryloxycarbonyloxy group,
preferably a substituted or unsubstituted aryloxycarbonyloxy group having a carbon number of 7 to 30 (e.g., phenoxycarbonyloxy, p-methoxyphenoxycarbonyloxy, p-n-hexadecyloxyphenoxycarbonyloxy),
(19) an amino group,
preferably an amino group, a substituted or unsubstituted alkylamino group having a carbon number of 1 to 30, a substituted or unsubstituted anilino group having a carbon number of 6 to 30 (e.g., amino, methylamino, dimethylamino, anilino, N-methyl-anilino, diphenylamino), or a heterocyclic amino group,
(20) an ammonio group,
preferably an ammonio group or an ammonio group substituted by a substituted or unsubstituted alkyl, aryl or heterocyclic group having a carbon number of 1 to 30 (e.g., trimethylammonio, triethylammonio, diphenylmethylammonio),
(21) an acylamino group,
preferably a formylamino group, a substituted or unsubstituted alkylcarbonylamino group having a carbon number of 2 to 30, or a substituted or unsubstituted arylcarbonylamino group having a carbon number of 7 to 30 (e.g., formylamino, acetylamino, pivaloylamino, lauroylamino, benzoylamino, 3,4,5-tri-n-octyloxyphenylcarbonylamino),
(22) an aminocarbonylamino group,
preferably a substituted or unsubstituted aminocarbonylamino group having a carbon number of 1 to 30 (e.g., carbamoylamino, N,N-dimethylaminocarbonylamino, N,N-diethylaminocarbonylamino, morpholinocarbonylamino),
(23) an alkoxycarbonylamino group,
preferably a substituted or unsubstituted alkoxycarbonylamino group having a carbon number of 2 to 30 (e.g., methoxycarbonylamino, ethoxycarbonylamino, tert-butoxycarbonylamino, n-octadecyloxycarbonylamino, N-methylmethoxycarbonylamino),
(24) an aryloxycarbonylamino group,
preferably a substituted or unsubstituted aryloxycarbonylamino group having a carbon number of 7 to 30 (e.g., phenoxycarbonylamino, p-chlorophenoxycarbonylamino, m-n-octyloxyphenoxycarbonylamino)),
(25) a sulfamoylamino group,
preferably a substituted or unsubstituted sulfamoylamino group having a carbon number of 0 to 30 (e.g., sulfamoylamino, N,N-dimethylaminosulfonylamino, N-n-octylaminosulfonylamino),
(26) an alkyl- or aryl-sulfonylamino group,
preferably a substituted or unsubstituted alkylsulfonylamino group having a carbon number of 1 to 30, or a substituted or unsubstituted arylsulfonylamino group having a carbon number of 6 to 30 (e.g., methylsulfonylamino, butylsulfonylamino, phenylsulfonylamino, 2,3,5-trichlorophenylsulfonylamino, p-methylphenylsulfonylamino),

(27) a mercapto group,
(28) an alkylthio group,
preferably a substituted or unsubstituted alkylthio group having a carbon number of 1 to 30 (e.g., methylthio, ethylthio, n-hexadecylthio),
(29) an arylthio group,
preferably a substituted or unsubstituted arylthio group having a carbon number of 6 to 30 (e.g., phenylthio, p-chlorophenylthio, m-methoxyphenylthio),
(30) a heterocyclic thio group,
preferably a substituted or unsubstituted heterocyclic thio group having a carbon number of 2 to 30 (e.g., 2-benzothiazolylthio, 1-phenyltetrazol-5-ylthio),
(31) a sulfamoyl group,
preferably a substituted or unsubstituted sulfamoyl group having a carbon number of 0 to 30 (e.g., N-ethylsulfamoyl, N-(3-dodecyloxypropyl)sulfamoyl, N,N-dimethylsulfamoyl, N-acetylsulfamoyl, N-benzoylsulfamoyl, N—(N'-phenylcarbamoyl)sulfamoyl),
(32) a sulfo group,
(33) an alkyl- or aryl-sulfinyl group,
preferably a substituted or unsubstituted alkylsulfinyl group having a carbon number of 1 to 30, or a substituted or unsubstituted arylsulfinyl group having a carbon number of 6 to 30 (e.g., methylsulfinyl, ethylsulfinyl, phenylsulfinyl, p-methylphenylsulfinyl),
(34) an alkyl- or aryl-sulfonyl group,
preferably a substituted or unsubstituted alkylsulfonyl group having a carbon number of 1 to 30, or a substituted or unsubstituted arylsulfonyl group having a carbon number of 6 to 30, e.g., methylsulfonyl, ethylsulfonyl, phenylsulfonyl, p-methylphenylsulfonyl,
(35) an acyl group,
preferably a formyl group, a substituted or unsubstituted alkylcarbonyl group having a carbon number of 2 to 30, a substituted or unsubstituted arylcarbonyl group having a carbon number of 7 to 30, or a substituted or unsubstituted heterocyclic carbonyl group having a carbon number of 4 to 30 and being bonded to a carbonyl group through a carbon atom (e.g., acetyl, pivaloyl, 2-chloroacetyl, stearoyl, benzoyl, p-n-octyloxyphenylcarbonyl, 2-pyridylcarbonyl, 2-furylcarbonyl),
(36) an aryloxycarbonyl group,
preferably a substituted or unsubstituted aryloxycarbonyl group having a carbon number of 7 to 30 (e.g., phenoxycarbonyl, o-chlorophenoxycarbonyl, m-nitrophenoxycarbonyl, p-tert-butylphenoxycarbonyl),
(37) an alkoxycarbonyl group,
preferably a substituted or unsubstituted alkoxycarbonyl group having a carbon number of 2 to 30 (e.g., methoxycarbonyl, ethoxycarbonyl, tert-butoxycarbonyl, n-octadecyloxycarbonyl),
(38) a carbamoyl group,
preferably a substituted or unsubstituted carbamoyl group having a carbon number of 1 to 30 (e.g., carbamoyl, N-methylcarbamoyl, N,N-dimethylcarbamoyl, N,N-di-n-octylcarbamoyl, N-(methylsulfonyl)carbamoyl),
(39) an aryl or heterocyclic azo group,
preferably a substituted or unsubstituted arylazo group having a carbon number of 6 to 30, or a substituted or unsubstituted heterocyclic azo group having a carbon number of 3 to 30 (e.g., phenylazo, p-chlorophenylazo, 5-ethylthio-1,3,4-thiadiazol-2-ylazo),
(40) an imido group,
preferably N-succinimido or N-phthalimido,
(41) a phosphino group,
preferably a substituted or unsubstituted phosphino group having a carbon number of 2 to 30 (e.g., dimethylphosphino, diphenylphosphino, methylphenoxyphosphino),
(42) a phosphinyl group,
preferably a substituted or unsubstituted phosphinyl group having a carbon number of 2 to 30 (e.g., phosphinyl, dioctyloxyphosphinyl, diethoxyphosphinyl),
(43) a phosphinyloxy group,
preferably a substituted or unsubstituted phosphinyloxy group having a carbon number of 2 to 30 (e.g., diphenoxyphosphinyloxy, dioctyloxyphosphinyloxy),
(44) a phosphinylamino group,
preferably a substituted or unsubstituted phosphinylamino group having a carbon number of 2 to 30 (e.g., dimethoxyphosphinylamino, dimethylaminophosphinylamino),
(45) a silyl group,
preferably a substituted or unsubstituted silyl group having a carbon number of 3 to 30 (e.g., trimethylsilyl, triethylsilyl, triisopropylsilyl, tert-butyldimethylsilyl, phenyldimethylsilyl), or
(46) a hydrazino group,
preferably a substituted or unsubstituted hydrazino group having a carbon number of 0 to 30 (e.g., trimethylhydrazino).

$R_1$ and $R_2$ each independently represents a substituent having a carbon number of 1 to 12 and may be selected from the above-described substituents W. In particular, the substituent is preferably a hydrocarbon group having a carbon number of 1 to 6, more preferably an alkyl group or an aryl group. This substituent may be further substituted by the substituent W.

The compound of formula (1) is preferably a compound of formula (2) where the description and preferred examples of $R_{21}$ and $R_{22}$ are the same as those of $R_1$ and $R_2$ in formula (1).

$R_{23}$, $R_{24}$, $R_{25}$ and $R_{26}$ include, for example, the substituents W but each is preferably a hydrocarbon group having a carbon number of 1 to 12, more preferably an alkyl group having a carbon number of 1 to 8 (e.g., methyl, ethyl, propyl, n-butyl, benzyl, phenethyl), still more preferably a methyl group, an ethyl group or a propyl group. A plurality of $R_{23}$'s, $R_{24}$'s, $R_{25}$'s or $R_{26}$'s may be the same or different but are preferably the same. The substituents $R_{23}$, $R_{24}$, $R_{25}$ and $R_{26}$ each may form a ring with $R_{21}$, $R_{22}$, $R_{23}$, $R_{24}$, $R_{25}$ or $R_{26}$ other than the substituent itself and preferably forms a ring (preferably a 5- or 6-membered ring) by a hydrocarbon chain.

$A_2$ and $B_2$ each independently represents a ring structure (forms a ring together with —C=C—). The ring formed is preferably an aromatic ring, and examples thereof include a benzene ring, a pyrrole ring, an oxazole ring, a thiazole ring, an imidazole ring, a pyridine ring, a pyrimidine ring and a pyridazine ring. Among these, a benzene ring and a pyridine ring are preferred, and a benzene ring is more preferred. In addition to the above-described ring structure, the ring structure is preferably a benzo-condensed ring (naphthalene ring), and these ring structures each may be further substituted by the substituent W.

Preferred examples of the squarylium compound of the present invention are set forth below.

Compound 1

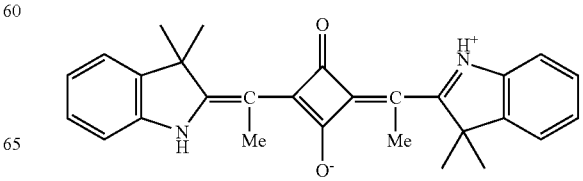

Compound 2
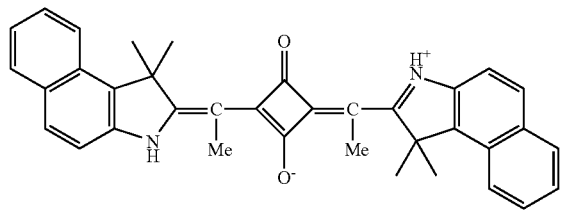
Compound 3
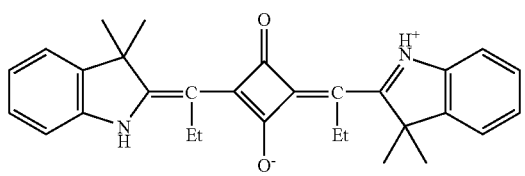
Compound 4
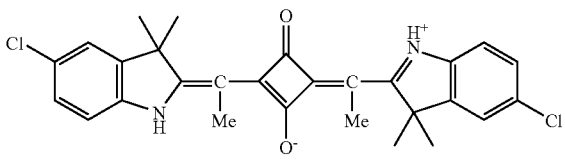
Compound 5
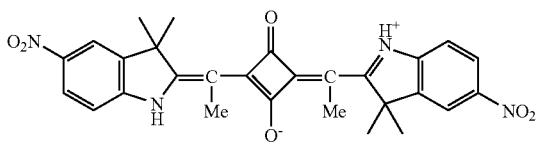
Compound 6
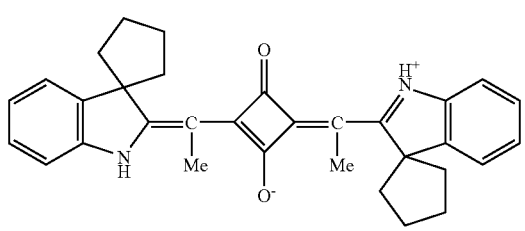
Compound 7
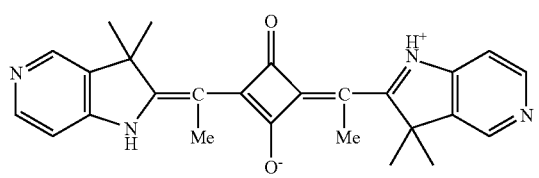
Compound 8
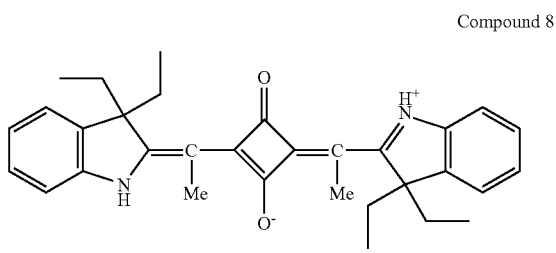
Compound 9
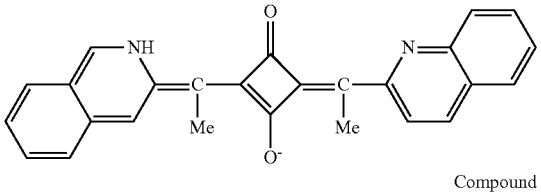
Compound 10
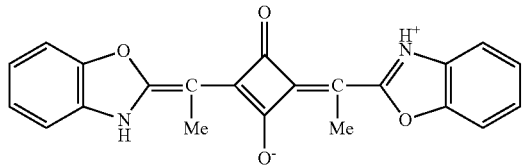
Compound 11
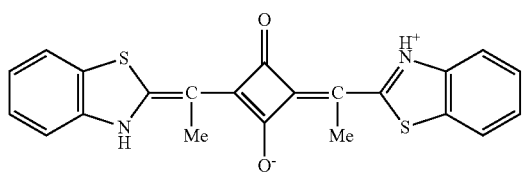
Compound 12
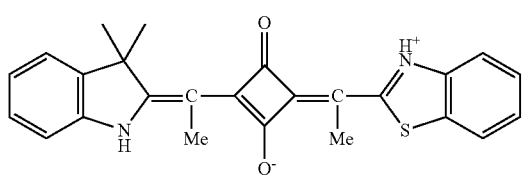
Compound 13
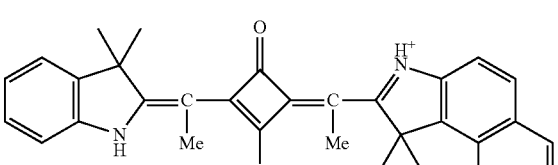
Compound 14
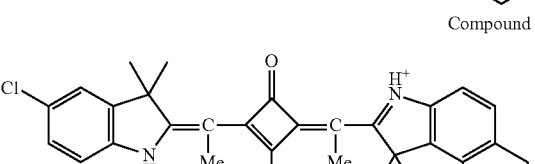
Compound 15
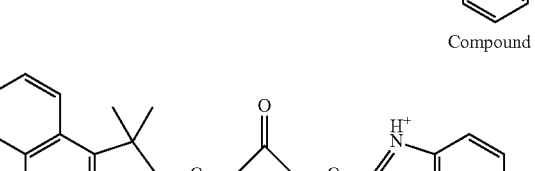
Compound 16
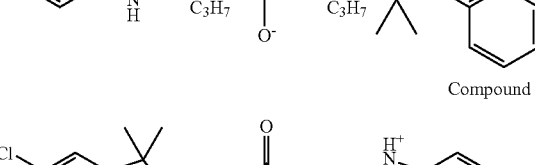

Compound 17

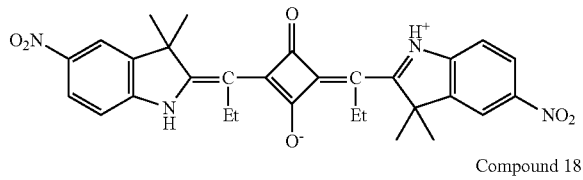

Compound 18

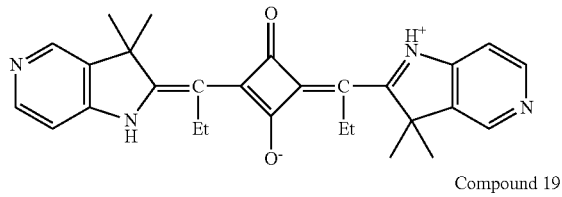

Compound 19

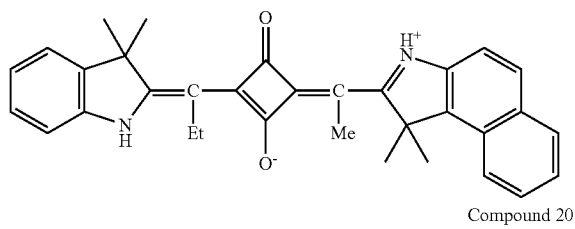

Compound 20

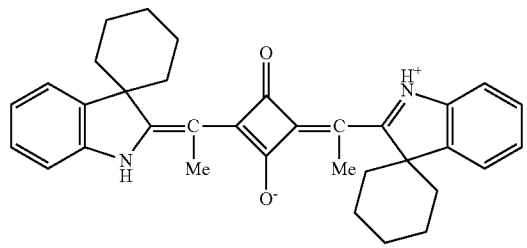

The compounds represented by formulae (1), (2), (5) and (6) and specific compounds each is indicated using one chemical formula, but the indication of a chemical formula in this field can take a resonance structure or the like and needless to say, those represented by other indications are also included in the present invention.

The compounds set forth above as specific examples can be synthesized by referring to known publications (e.g., *Dyes and Pigments*, 21, 227-234 (1993)).

A part of the compound represented by formulae (1) and (5) of the present invention is preferably produced using a compound represented by formula (3). A compound represented by formula (4) can be produced using a compound represented by formula (3). The compound represented by formula (3) is a heretofore unknown compound.

In the compounds represented by formulae (3) and (4), $R_{31}$ has the same meaning as $R_1$ in formula (1), and specific examples and preferred ranges are also the same. $R_{32}$ and $R_{33}$ each independently has the same meaning as $R_{23}$ and $R_{24}$ in formula (2), and specific examples and preferred ranges are also the same.

In the compound represented by formula (4), $B_1$ and $R_2$ have the same meanings as $B_1$ and $R_2$ in formula (1), and specific examples and preferred ranges are also the same as those in formula (1). Out of the compounds represented by formula (4) produced using a compound represented by formula (3), a compound represented by the following formula (7) is preferred, and a compound represented by formula (8) is more preferred. The production process thereof is realized according to the following scheme.

Formula (7):

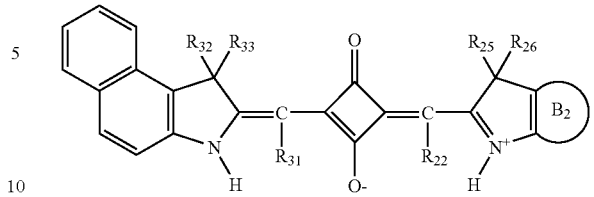

In the formula, $R_{31}$, $R_{32}$ and $R_{33}$ have the same meanings as those in formula (3), and specific examples and preferred ranges are also the same. $R_{22}$, $R_{25}$, $R_{26}$ and $B_2$ have the same meanings as those in formula (2), and specific examples and preferred ranges are also the same.

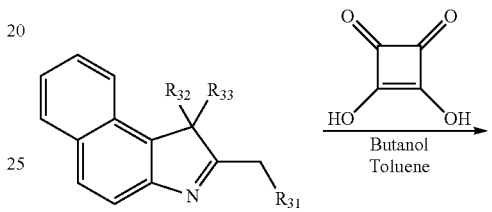

Formula (3)

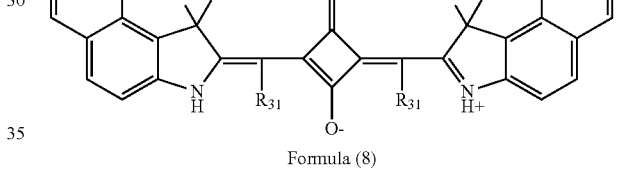

Formula (8)

(wherein $R_{31}$ has the same meaning as $R_1$ in formulae (1) and (5), and $R_{32}$ and $R_{33}$ each independently has the same meaning as $R_{23}$ and $R_{24}$ in formulae (2) and (6)).

$R_{31}$, $R_{32}$ and $R_{33}$ each is independently preferably an alkyl group having a carbon number of 1 to 12, or an aryl group having a carbon number of 6 to 12, more preferably a methyl group, an ethyl group, a propyl group or a butyl group, and $R_{31}$, $R_{32}$ and $R_{33}$ may combine to form a ring.

In the production process for use in the present invention, a mixture of alcohols and a hydrocarbon-based solvent is preferably used as the solvent. Examples of the alcohols include methanol, ethanol, propanol, butanol and hexanol, and examples of the hydrocarbon-based solvent include toluene, benzene, xylene, mesitylene, n-hexane and cyclohexane. The reaction temperature is preferably from room temperature to 300° C., more preferably from 100 to 200° C. The reaction may be performed at the boiling point of the solvent. Also when an acid catalyst or a base catalyst is allowed to be present together during the reaction, good results are obtained.

The method of forming an organic film includes, for example, a coating method such as spin coating, and a vapor deposition method of vaporizing a material under heating in vacuum and depositing it on a base, but in view of preventing intermingling of impurities and favoring wide latitude in forming multiple layers so as to achieve high functionality, a vapor deposition method is preferred. The vapor deposition apparatus may be a commercially available apparatus, but the temperature of the vapor deposition source during vapor deposition is preferably from 100 to 500° C., more preferably from 150 to 400° C. The degree of vacuum at the vapor deposition is preferably from 1 to $1\times10^{-4}$ Pa, more preferably from 0.1 to $1\times10^{-3}$ Pa. A method of increasing the vapor deposition rate by adding a metal fine particle or the like to the vapor deposition source is also preferably used.

A chroconium or cyanine-based dye representative of a dye having absorption in the infrared region has a low decomposition temperature and a high vapor deposition temperature and therefore, readily decomposes due to heating at the vapor deposition and a film can be hardly formed. Accordingly, a dye having a high decomposition temperature and a low vapor deposition temperature is preferred. The decomposition temperature can be measured by a known thermal analysis such as TG-DTA. In the present invention, the temperature at which reduction in the mass occurs as a result of the TG-DTA measurement in nitrogen is defined as the decomposition initiating temperature. The vapor deposition temperature is defined as a temperature at which a dye deposits on a substrate when a sample is heated in vacuum in a vapor deposition apparatus while measuring the temperature by a quartz oscillator. The squarylium dye of the present invention preferably has a vapor deposition temperature higher than the decomposition initiating temperature, by 30° C. or more, more preferably by 50° C. or more.

The thin-film properties of the dye are described below. The infrared dye thin film is preferably a thin film having a large absorption intensity in the infrared region and a small absorption intensity in the visible region. The absorption intensity in the visible region may be increased by mixing other dyes but cannot be decreased, and therefore, smallness of the absorption intensity is important. The main absorption is, in terms of the absorption maximum wavelength, preferably 700 nm or more, more preferably 750 nm or more. As for the absorption intensity in the visible region, the maximum value of the relative absorbance to the main absorption at 400 to 550 nm is preferably 0.15 or less, more preferably 0.1 or less.

As for the principal construction of the photoelectric conversion element of the present invention, this photoelectric conversion element is a photoelectric conversion element comprising a photoelectric conversion part containing a pair of electrodes and a photoelectric conversion film provided between the pair of electrode, wherein the photoelectric conversion film comprises an organic photoelectric conversion material and the organic photoelectric conversion material comprises a compound represented by formula (1).

The photoelectric conversion element having a photoelectric conversion part containing a photoelectric conversion film comprising a compound represented by formulae (1), (2), (5) or (6) as an organic photoelectric conversion material is described below.

The embodiments of the photoelectric conversion element of the present invention are described below by referring to the drawings. In the following, the light (R light) in the red (R) wavelength region indicates light at a wavelength of 550 to 650 nm, the light (G light) in the green (G) wavelength region indicates light at a wavelength of 450 to 610 nm, the light (B light) in the blue (B) wavelength region indicates light at a wavelength of 400 to 520 nm, the light (infrared light) in the infrared wavelength region indicates light at a wavelength of 680 to 10,000 nm, and the light (visible light) in the visible wavelength region indicates light at a wavelength of 400 to 650 nm.

First Embodiment of Photoelectric Conversion Element

Figure 11:
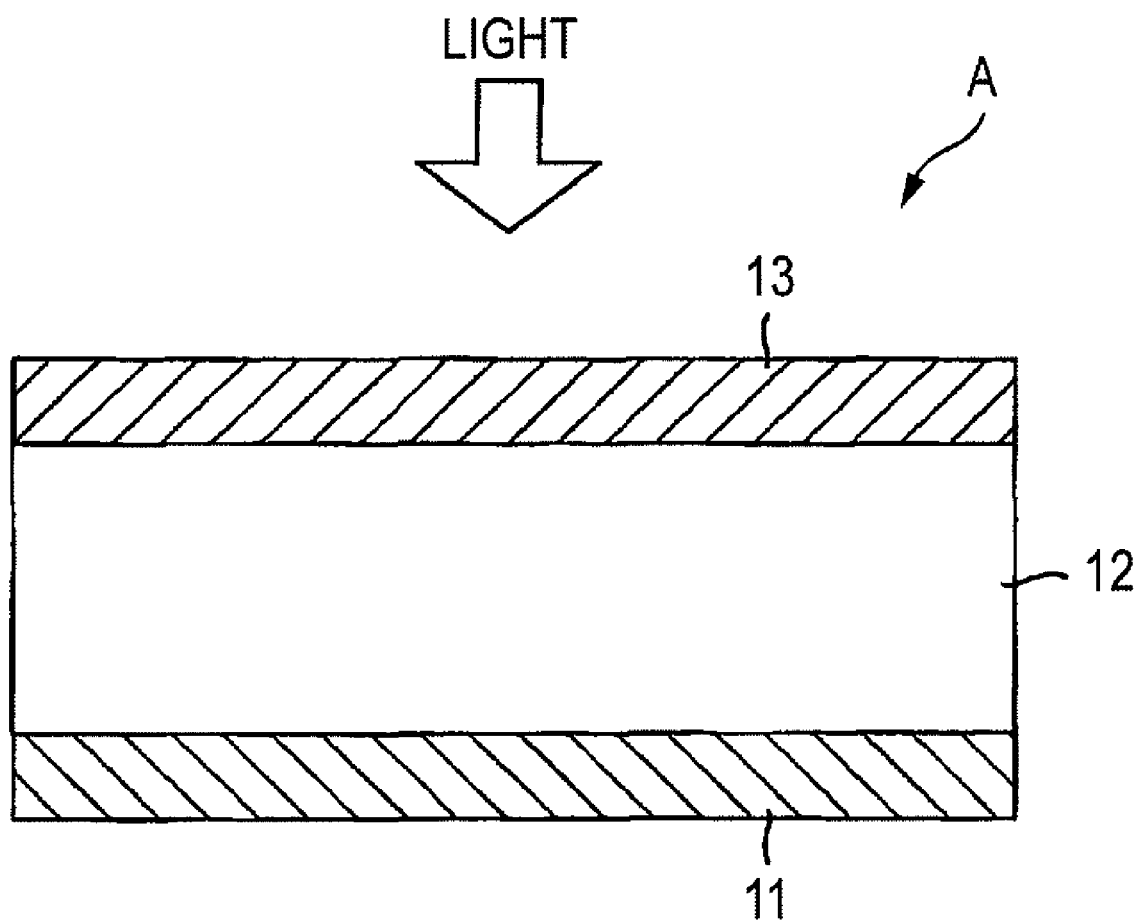
FIG. 11 is a cross-sectional schematic view roughly showing the construction of the photoelectric conversion element in the first embodiment of the present invention.

FIG. 11 is a cross-sectional schematic view roughly showing the construction of the photoelectric conversion element in the first embodiment of the present invention.

The photoelectric conversion element shown in FIG. 11 comprises at least a photoelectric conversion part A containing a lower electrode 11, an upper electrode 13 facing the lower electrode 11, and a photoelectric conversion film 12 provided between the lower electrode 11 and the upper electrode 13. The photoelectric conversion element shown in FIG. 11 is used by making light incident from the upper side of the upper electrode 13.

The upper electrode 13 is a transparent electrode composed of an electrically conductive material transparent to light (visible light and infrared light) in the combined range of a visible region and an infrared region (the range at a wavelength of 400 nm or more). A bias voltage is applied to the upper electrode 13 through wiring not shown. The polarity of this bias voltage is determined such that out of electric charges generated in the photoelectric conversion film 12, an electron moves to the upper electrode 13 and a hole moves to the lower electrode 11. Of course, the bias voltage may be set such that out of electric charges generated in the photoelectric conversion film 12, a hole moves to the upper electrode 13 and an electron moves to the upper electrode 11. As for the bias voltage, the value obtained by dividing the bias voltage value by the distance between the lower electrode 11 and the upper electrode 13 is preferably from $1.0\times10^5$ to $1.0\times10^7$ V/cm, more preferably from $1.0\times10^4$ to $1.0\times10^6$ V/cm. With the bias voltage in this range, an electric charge can be efficiently moved to the upper electrode 13, and a signal according to this electric charge can be taken outside.

For the application to a solid-state imaging device capable of simultaneously performing the photographing of a visible image and the photographing of an infrared image (hereinafter referred to as a "visible/infrared imaging device"), a transparent electrode is preferably used for the lower electrode 11 similarly to the upper electrode 11, because out of the incident light, visible light must be transmitted to the lower side thereof. However, the lower electrode 11 need not be transparent to light in the infrared region and may be sufficient if it is transparent at least to light in the visible region.

The photoelectric conversion film 12 is a film comprising an organic photoelectric conversion material which has an absorption peak in the infrared region of the absorption spectrum in the combined range of a visible region and an infrared region (light at a wavelength of 400 nm or more) and generates an electric charge according to the infrared light absorbed.

As for such an organic photoelectric conversion material, the above-described squarylium-based dye is preferably used.

In the case of applying the thus-constructed photoelectric conversion element having a photoelectric conversion part A to a visible/infrared imaging device, for allowing the photoelectric conversion part A to obtain information other than the human visibility, the absorption peak in the infrared region of the organic photoelectric conversion material contained in the photoelectric conversion film 12 is preferably present at a wavelength of 700 nm or more, more preferably 730 nm or more.

The photoelectric conversion element of the present invention is preferably transparent to visible light and therefore, in the absorption spectrum in the combined range of a visible region and an infrared region, the relative value of the maximum absorbance at 400 to 650 nm where the visibility is high, with respect to the absorbance at the absorption maximum wavelength is preferably 0.8 or less, more preferably 0.7 or less.

The photoelectric conversion element of the present invention preferably has sensitivity to infrared light and therefore, preferably exhibits high external quantum efficiency for light at 700 nm or more. Examples of the wavelength of infrared light include 720 nm and 800 nm.

The visible light transmittance of the photoelectric conversion part A can be adjusted by appropriately selecting the construction material and thickness of each of the upper electrode 13, the lower electrode 11 and the photoelectric conversion film 12.

The "absorptance or transmittance in a certain wavelength region of α to β nm" as used in the present invention is defined as "a value which can be expressed by Y/X×100 where assuming that the absorptance or transmittance in the wavelength region of α to β nm is 100%, X is the integration value in the wavelength region of α to β nm and Y is the integration value of the absorptance or transmittance at each wavelength in the wavelength region of α to β nm."

The light transparency of the lower electrode 11 or upper electrode 13 greatly affects the infrared light absorptance and visible light absorptance of the underlayer thereof. When the incident light is absorbed or reflected in the lower electrode 11 or upper electrode 13, the absolute quantity of light reaching the underlayer decreases and this leads directly to reduction in the sensitivity. In order to transmit a larger quantity of light to the underlayer and increase the sensitivity in the photoelectric conversion film 12, the transmittance of the upper electrode 13 for visible light and infrared light is preferably 90% or more, more preferably 95% or more. Also, in order to transmit a larger quantity of visible light to the underlayer and increase the sensitivity in a visible light detecting element provided on the lower side of the photoelectric conversion element, the visible light transmittance of the lower electrode 11 is preferably 90% or more, more preferably 95% or more.

As for the material of the lower electrode 11 and upper electrode 13 satisfying these conditions, a transparent electrically conductive oxide (TCO; transparent conducting oxide) exhibiting high transmittance for visible light and infrared light and having a small resistance value can be preferably used. A metal thin film of Au or the like may be used, but when a transmittance of 90% or more is intended to obtain, the resistance value extremely increases. Therefore, TCO is preferred. Examples of TCO which can be preferably used include ITO, IZO, AZO, FTO, $SnO_2$, $TiO_2$ and $ZnO_2$.

In the case of film-forming a transparent electrically conductive material such as TCO on the photoelectric conversion film 12 to form the upper electrode 13, a DC short or an increase of leak current is sometimes brought about. One of causes thereof is considered because fine cracks introduced into the photoelectric conversion film 12 are coveraged by a dense film of TCO or the like and conduction with the transparent electrically conductive material film on the opposite side increases. Therefore, in the case of an electrode having relatively poor film quality such as Al, the leak current less increases. The increase of leak current can be greatly suppressed by controlling the thickness of the transparent electrically conductive material film with respect to the thickness (that is, the crack depth) of the photoelectric conversion film 12. The thickness of the transparent electrically conductive material film, that is, the thickness of the upper electrode 13, is preferably ⅕ or less, preferably ¹⁄₁₀ or less, of the thickness of the photoelectric conversion film 12.

Usually, when the thickness of the transparent electrically conductive material film is made smaller than a certain range, an abrupt increase of the resistance value is brought about, but in the photoelectric conversion element of the present invention, the sheet resistance may be preferably from 100 to 10,000 Ω/sq. and the latitude as to in which range the film thickness can be reduced is large. Also, as the thickness of the transparent electrically conductive material film is smaller, the quantity of light absorbed becomes small and the light transmittance is generally increased. The increase of transmittance brings about an increase of light absorption in the photoelectric conversion film 12 and an increase of photoelectric conversion performance, and this is very preferred. Considering the suppression of leak current as well as the increase of resistance value of thin film and increase of transmittance, which are favored by reducing the thickness of the transparent electrically conductive material film, the transparent electrically conductive material film preferably has a thickness of 5 to 100 nm, more preferably from 5 to 20 nm.

In the case where irregularities are present on the lower electrode 11 surface or dusts are adhering to the lower electrode 11 surface and where a low molecular organic photoelectric conversion material is vapor-deposited thereon to form the photoelectric conversion film 12, the irregularity portion is liable to allow for production of fine cracks in the photoelectric conversion film 12 or only thin formation of the photoelectric conversion film 12. At this time, when the upper electrode 13 is further formed thereon, the cracks are coveraged by the transparent electrically conductive material film, and the photoelectric conversion film 12 and the upper electrode 13 are partially put into proximity, as a result, a DC short or an increase of leak current is readily caused. This tendency is prominent particularly when TCO is used as the upper electrode 13. As one method for preventing such an increase of leak current, a subbing film for alleviating the irregularities is preferably formed on the lower electrode 11. As for the subbing film, when a method of forming the film by spin-coating a polymer-based material such as polyaniline, polythiophene, polypyrrole, polycarbazole, PTPDES and PTPDEK is used, the effect is great. In the case of forming the photoelectric conversion film 12 in vacuum by a vapor deposition method or the like so as to prevent intermingling of impurities and more facilitate the production of a uniform stack film, an amorphous film is preferably used as the subbing layer.

With respect to the combination of a lower electrode 11, an organic photoelectric conversion material and an upper electrode 13, which enables the photoelectric conversion part A to have a visible light transmittance of 50% or more, as described later in Examples, there may be considered a combination where the lower electrode 11 and the upper electrode 13 each is ITO and the organic photoelectric conversion material is tin phthalocyanine. Other than this combination, when the lower electrode 11 and the upper electrode 13 each is IZO, AZO, FTO, $SnO_2$, $TiO_2$ or $ZnO_2$ and the organic photoelectric conversion material is any one of the above-described dyes, a photoelectric conversion part A having a visible light transmittance of 50% or more can be realized.

Second Embodiment of Photoelectric Conversion Element

FIG. 12 is a cross-sectional schematic view roughly showing the construction of the photoelectric conversion element in the second embodiment of the present invention.

Figure 12A:
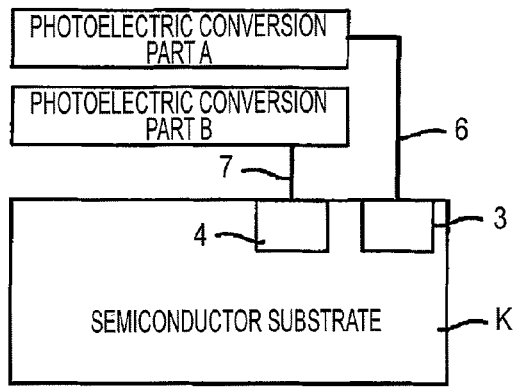
FIGS. 12A to 12D are cross-sectional schematic views roughly showing the construction of the photoelectric conversion element in the second embodiment of the present invention.

The photoelectric conversion element shown in FIG. 12A comprises a semiconductor substrate K such as silicon, a visible light photoelectric conversion part B stacked on the upper side of the semiconductor substrate K, and the photoelectric conversion part A shown in FIG. 11 stacked on the upper side of the visible light photoelectric conversion part B.

The visible light photoelectric conversion part B has almost the same construction as the photoelectric conversion part A and as for the organic photoelectric conversion material constituting the photoelectric conversion film 12 of the photoelectric conversion part A, a material having an absorption peak in the visible region of the absorption spectrum in the combined range of a visible region and an infrared region (the range at a wavelength of 400 nm or more) and generating an electric charge according to the light absorbed is used.

In the semiconductor substrate K, an accumulation part 3 for accumulating an electric charge generated in the photoelectric conversion film 12 of the photoelectric conversion part A and moved to the upper electrode 13 is formed, and this accumulation part 3 and the upper electrode 13 are electrically connected by a connection part 6. Also, in the semiconductor substrate K, an accumulation part 4 for accumulating an electric charge generated in the photoelectric conversion film of the photoelectric conversion part B and moved to the upper electrode is formed, and this accumulation part 4 and the upper electrode are electrically connected by a connection part 7.

Figure 12B:
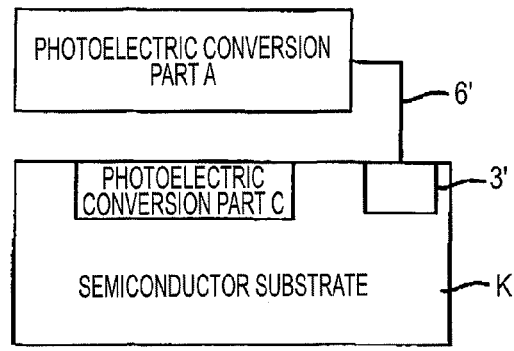

The photoelectric conversion element shown in FIG. 12B comprises a semiconductor substrate K such as silicon and the photoelectric conversion part A shown in FIG. 11 stacked on the upper side of the semiconductor substrate K. In the semiconductor substrate K on the lower side of the photoelectric conversion part A, a visible light photoelectric conversion part C having an absorption peak in the visible region of the absorption spectrum in the combined range of a visible region and an infrared region (the range at a wavelength of 400 nm or more) and generating an electric charge according to the light absorbed is formed. Also, in the semiconductor substrate K, an accumulation part 3' for accumulating an electric charge generated in the photoelectric conversion film 12 of the photoelectric conversion part A and moved to the upper electrode 13 is formed, and this accumulation part 3' and the upper electrode 13 are electrically connected by a connection part 6'. The visible light photoelectric conversion part C is composed of, for example, a known pn-junction photodiode.

By virtue of the constructions shown in FIGS. 12A and 12B, a photoelectric conversion element capable of acquiring a signal according to infrared light by an electric charge generated in the photoelectric conversion part A provided as the upper layer and acquiring a signal according to visible light by an electric charge generated in the photoelectric conversion part B or photoelectric conversion part C provided on the lower side of the photoelectric conversion part A can be realized.

In the case of the construction of FIG. 12A, for example, by forming the photoelectric conversion film of the photoelectric conversion part B from a quinacridone-based organic material (e.g., quinacridone), a signal according to infrared light and a signal according to G light can be acquired at the same time. Accordingly, when many photoelectric conversion elements of FIG. 12A are two-dimensionally arrayed on the same plane and a signal read-out circuit such as CCD or CMOS circuit for reading out a signal according to an electric charge generated in each photoelectric conversion element is provided in the semiconductor substrate K, an infrared/visible imaging device capable of simultaneously photographing an infrared image according to infrared light and a black-and-white image according to G light can be realized.

Also, when many photoelectric conversion elements fabricated by forming the photoelectric conversion film of the photoelectric conversion part B from a quinacridone-based organic material (e.g., quinacridone), many photoelectric conversion elements fabricated by forming the photoelectric conversion film of the photoelectric conversion part B from a phthalocyanine-based organic material (e.g., zinc phthalocyanine), and many photoelectric conversion elements fabricated by forming the photoelectric conversion film of the photoelectric conversion part B from a porphyrin-based organic material are two-dimensionally arrayed in the same plane and a signal read-out circuit such as CCD or CMOS circuit for reading out a signal according to an electric charge generated in each photoelectric conversion element is provided in the semiconductor substrate K, an infrared/visible imaging device capable of simultaneously photographing an infrared image according to infrared light and a color image according to R, G and B lights through known signal processing can be realized.

In addition, in FIG. 12A, by further providing two photoelectric conversion parts B between the photoelectric conversion part A and the photoelectric conversion part B or between the semiconductor substrate K and the photoelectric conversion part B and forming the photoelectric conversion films of three photoelectric conversion parts B in total from quinacridone, zinc phthalocyanine and a porphyrin-based organic compound, respectively, a signal according to infrared light can be acquired from the photoelectric conversion part A and signals according to R, G and B lights can be acquired from those three photoelectric conversion parts B. Therefore, when many photoelectric conversion elements of FIG. 12A are two-dimensionally arrayed on the same plane and a signal read-out circuit such as CCD or CMOS circuit for reading out a signal according to an electric charge generated in each photoelectric conversion element is provided in the semiconductor substrate K, an infrared/visible imaging device capable of simultaneously photographing an infrared image according to infrared light and color image according to R, G and B lights can be realized. Of course, a construction where one photoelectric conversion part B or three or more photoelectric conversion parts B are provided between the photoelectric conversion part A and the photoelectric conversion part B or between the semiconductor substrate K and the photoelectric conversion part B can also be employed depending on the usage.

In the case of the construction of FIG. 12B, the photoelectric conversion part C itself is a pn-junction photodiode fundamentally having sensitivity to light at a wavelength of 1,100 nm or less and therefore, has sensitivity to light other than the infrared light absorbed by the photoelectric conversion part A. When there is no light-absorbing part other than the photoelectric conversion part A, the light entering the photoelectric conversion part C becomes the entire light at wavelengths transmitted through the photoelectric conversion part A, and a signal according to infrared light and a signal according to visible light can be simultaneously acquired. Therefore, when many photoelectric conversion elements of FIG. 12B are two-dimensionally arrayed on the same plane and a signal read-out circuit such as CCD or CMOS circuit for reading out a signal according to an electric charge generated in each photoelectric conversion element is provided in the semiconductor substrate K, an infrared/visible imaging device capable of simultaneously photographing an infrared image according to infrared light and a black-and-white image according to visible light can be realized.

With respect to the photoelectric conversion part C, as described in U.S. Pat. No. 5,965,875, when an imaging device is fabricated by forming a pn-junction face at each of an R light absorption depth, a G light absorption depth and a B light absorption depth and stacking three photoelectric conversion parts C in the depth direction such that the wavelength absorbed is separated in the silicon depth direction to acquire a signal corresponding to each absorption wavelength, a color signal can be acquired from the visible light transmitted through the photoelectric conversion part A, and a signal according to infrared light and signals according to R, G and B lights can be acquired at the same time. Of course, a construction where two photoelectric conversion parts C or four or more photoelectric conversion parts C are provided in the semiconductor substrate K on the lower side of the photoelectric conversion part A can also be employed depending on the usage.

Furthermore, when a spectral filter transparent to light in a specific wavelength region is disposed on the upper side of the photoelectric conversion part A, the light allowed to enter the photoelectric conversion part C can be separated. As for the spectral filter, a primary color or complementary color filter used in a normal CCD or CMOS color image sensor can be employed. The color filter used in a CCD or CMOS color image sensor generally has a property of transmitting also a part of infrared light and therefore, even when the color filter is disposed on the upper side of the photoelectric conversion part A, infrared light can be made to enter the photoelectric conversion part A.

For example, when many photoelectric conversion elements where an R color filter capable of transmitting R light and a part of infrared light is provided on the upper side of the photoelectric conversion part A of FIG. 12B, many photoelectric conversion elements where a G color filter capable of transmitting G light and a part of infrared light is provided on the upper side of the photoelectric conversion part A of FIG. 12B, and many photoelectric conversion elements where a B color filter capable of transmitting B light and a part of infrared light is provided on the upper side of the photoelectric conversion part A of FIG. 12B, are arrayed on the same plane and a signal read-out circuit such as CCD or CMOS circuit for reading out a signal according to an electric charge generated in each photoelectric conversion element is provided in the semiconductor substrate K, an infrared/visible imaging device capable of simultaneously photographing an infrared image and a color image through known signal processing can be realized.

According to the photoelectric conversion elements shown in FIGS. 12A and 12B, photographic conversion parts for detecting different lights are stacked in the longitudinal direction, so that as compared with a normal color filter mode, almost all incident light can be taken out as a signal and by virtue of no loss in the light quantity, high sensitivity can be realized. Furthermore, in a normal Si photoelectric conversion device, an infrared cut filter is provided for cutting a signal based on infrared light, but the role thereof can be partially or entirely fulfilled by the photoelectric conversion part A as the uppermost layer and therefore, when applied to an imaging device, an effect of partially eliminating the use of an infrared cut filter can be obtained.

Figure 12C:
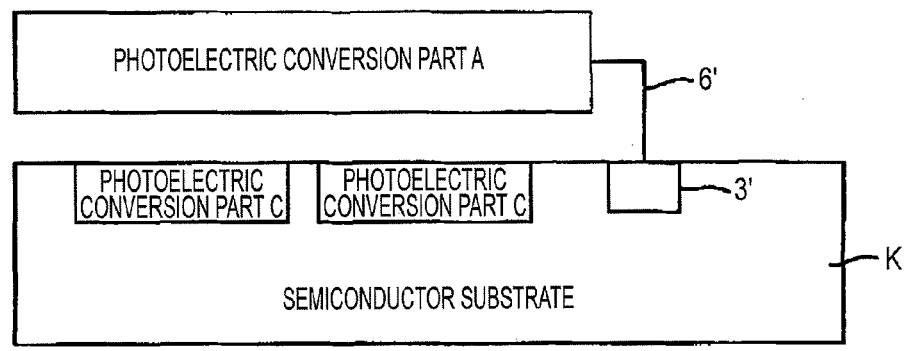

Incidentally, in FIGS. 12A and 12B, one or more photoelectric conversion parts B or photoelectric conversion parts C are stacked on the lower side of the photoelectric conversion part A, but a construction where, as shown in FIG. 12C, a plurality of photoelectric conversion parts C are formed in the semiconductor substrate K on the lower side of the photoelectric conversion part A and arrayed in the vertical direction (the direction parallel to the semiconductor substrate K surface) with respect to the incident direction of light entering the semiconductor substrate K, may also be considered. For example, three pn-junction photodiodes are formed as the photoelectric conversion part C in the semiconductor substrate K on the lower side of the photoelectric conversion part A and arrayed in the above-described vertical direction, and an R color filter, a G color filter and a B color filter are disposed on these three pn-junction photodiodes, respectively. Then, a large number of such photoelectric conversion elements are disposed on the same plane, and a signal read-out circuit such as CCD or CMOS circuit for reading out a signal according to an electric charge generated in each photoelectric conversion element is provided in the semiconductor substrate K, whereby an infrared/visible imaging device provided with a one-to-one correspondence between each photoelectric conversion element and a pixel and capable of simultaneously photographing an infrared image and a color image can be realized.

Different pixel sizes may be assigned to the photoelectric conversion part A and the photoelectric conversion part B or C.

Figure 12D:
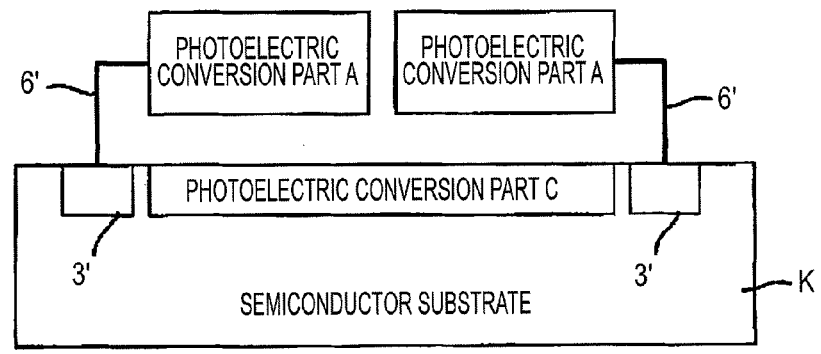

In FIG. 12C, a plurality of photoelectric conversion parts C are disposed to correspond to one photoelectric conversion part A, but it is also possible to employ an embodiment of allocating the plurality of conversion parts for the incident side and the one conversion part for the substrate side, or depending on the usage, as shown in FIG. 12D, to fabricate a construction where one photoelectric conversion part C corresponds to two photoelectric conversion parts A.

Incidentally, in the construction example shown in FIG. 12, as regards the photoelectric conversion part A and the photoelectric conversion part B, the photoelectric conversion part A and the photoelectric conversion part B are of course overlapped as viewed in plane such that light transmitted through the photoelectric conversion part A enters the photoelectric conversion part B. Similarly, as regards the photoelectric conversion part A and the photoelectric conversion part C, the photoelectric conversion part A and the photoelectric conversion part C are of course overlapped as viewed in plane such that light transmitted through the photoelectric conversion part A enters the photoelectric conversion part C.

Figure 13:
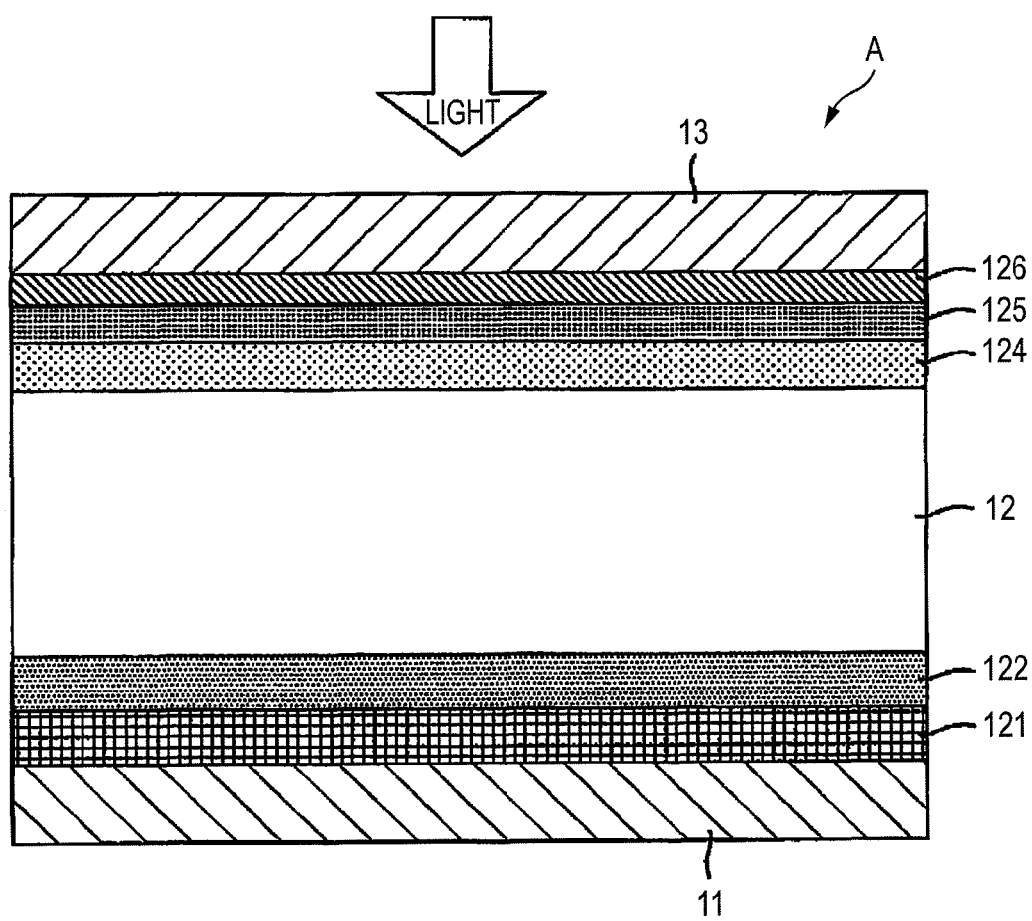
FIG. 13 is a cross-sectional schematic view showing a preferred embodiment of the photoelectric conversion element in the first embodiment of the present invention.

A more preferred embodiment of the photoelectric conversion part A shown in FIG. 11 is described below. The photoelectric conversion part A described here has a construction shown in FIG. 13. In FIG. 13, the same constituents as in FIG. 11 are denoted by like reference numerals.

The method for applying a voltage or the construction of element materials is preferably performed such that in the photoelectric conversion part A, a signal electric charge having lower performance of transporting a hole and an electron in the organic film is collected from the upper electrode 13 side on the light incident side, because the photoelectric conversion efficiency is high and the spectral sensitivity becomes sharp. In the photoelectric conversion film 12 of the photoelectric conversion part A, light absorption occurs mainly on the light incident side and therefore, when an electric charge having lower transport performance is collected from the upper electrode 13 closer to the light incident side, the charge transport distance becomes short and this enables reducing the deactivation of the electric charge during transport and increasing the efficiency. If the above-described direction in which the electric charge is collected is reversed, as the wavelength absorptance is larger, the electric charge generation part becomes closer to the upper electrode 13 side and the transport distance becomes longer, so that an electric charge can be hardly collected. Also, in the case of a wavelength of low absorptance allowing light to reach the back of film, the site generating an electric charge comes to locate in the back of film and the collection efficiency increases because of the short transport distance, as a result, the spectral sensitivity becomes broad with respect to the original absorption spectrum. Many materials for the organic film have a high hole transport ability and in this case, a mode of applying a voltage to collect an electron from the upper electrode 13, collecting a hole from the lower electrode 11, and accumulating, transferring and reading out a signal is preferred.

In the following, a case of collecting an electron from the upper electrode 13 is described. In the case of collecting a hole from the upper electrode 13, this may be attained by reversing the order of film formation except for a subbing film 121 and a work function adjusting film 126. As for the subbing film 121, the material may be selected or depending on the case, changed by taking into consideration the transport performance, and as for the work function adjusting film 126, a material having a large work function may be selected.

It is preferred to provide, as shown in FIG. 13, a subbing film 121 and an electron blocking film 122 between the photoelectric conversion film 12 and the lower electrode 11 of the photoelectric conversion part A and provide a hole blocking film 124, a hole blocking and buffer film 125 and a work function adjusting film 126 between the photoelectric conversion film 12 and the upper electrode 13.

The organic photoelectric conversion material constituting the photoelectric conversion film 12 preferably contains at least either an organic p-type semiconductor or an organic n-type semiconductor.

The organic p-type semiconductor (compound) is a donor organic semiconductor (compound) mainly typified by a hole-transporting organic compound and indicates an organic compound having a property of readily donating an electron, more specifically, an organic compound having a smaller ionization potential when two organic materials are used in contact. Accordingly, the donor organic compound may be any organic compound as long as it is an organic compound having an electron donating property. Examples of the compound which can be used include a triarylamine compound, a benzidine compound, a pyrazoline compound, a styrylamine compound, a hydrazone compound, a triphenylmethane compound, a carbazole compound, a polysilane compound, a thiophene compound, a phthalocyanine compound, a cyanine compound, a merocyanine compound, an oxonol compound, a polyamine compound, an indole compound, a pyrrole compound, a pyrazole compound, a polyarylene compound, a condensed aromatic carbocyclic compound (e.g., naphthalene derivative, anthracene derivative, phenanthrene derivative, tetracene derivative, pyrene derivative, perylene derivative, fluoranthene derivative), and a metal complex having a nitrogen-containing heterocyclic compound as a ligand. The donor organic semiconductor is not limited to these compounds and, as described above, an organic compound having an ionization potential smaller than that of the organic compound used as an n-type (acceptor) compound may be used as the donor organic semiconductor.

The organic n-type semiconductor (compound) is an acceptor organic semiconductor (compound) mainly typified by an electron-transporting organic compound and indicates an organic compound having a property of readily accepting an electron, more specifically, an organic compound having a larger electron affinity when two organic compounds are used in contact. Accordingly, as for the acceptor organic compound, any organic compound can be used as long as it is an organic compound having an electron accepting property. Examples thereof include a condensed aromatic carbocyclic compound (e.g., naphthalene derivative, anthracene derivative, phenanthrene derivative, tetracene derivative, pyrene derivative, perylene derivative, fluoranthene derivative), a 5- to 7-membered heterocyclic compound containing a nitrogen atom, an oxygen atom or a sulfur atom (e.g., pyridine, pyrazine, pyrimidine, pyridazine, triazine, quinoline, quinoxaline, quinazoline, phthalazine, cinnoline, isoquinoline, pteridine, acridine, phenazine, phenanthroline, tetrazole, pyrazole, imidazole, thiazole, oxazole, indazole, benzimidazole, benzotriazole, benzoxazole, benzothiazole, carbazole, purine, triazolopyridazine, triazolopyrimidine, tetrazaindene, oxadiazole, imidazopyridine, pyralidine, pyrrolopyridine, thiadiazolopyridine, dibenzazepine, tribenzazepine), a polyarylene compound, a fluorene compound, a cyclopentadiene compound, a silyl compound, and a metal complex having a nitrogen-containing heterocyclic compound as a ligand. The acceptor organic semiconductor is not limited to these compounds, and an organic compound having a larger electron affinity than the organic compound used as the donor organic compound may be used.

The metal complex compound is described below. The metal complex compound is a metal complex having at least one ligand containing a nitrogen, oxygen or sulfur atom coordinated to a metal. The metal ion in the metal complex is not particularly limited but is preferably beryllium ion, magnesium ion, aluminum ion, gallium ion, zinc ion, indium ion or tin ion, more preferably beryllium ion, aluminum ion, gallium ion or zinc ion, still more preferably aluminum ion or zinc ion. The ligand contained in the metal complex includes various known ligands, but examples thereof include ligands disclosed in H. Yersin, *Photochemistry and Photophysics of Coordination Compounds*, Springer-Verlag (1987), and Akio Yamamoto, *Yuki Kinzoku Kagaku—Kiso to Oyo—(Organic Metal Chemistry—Foundation and Application—)*, Shokabo (1982).

The ligand is preferably a nitrogen-containing heterocyclic ligand (preferably having a carbon number of 1 to 30, more preferably from 2 to 20, still more preferably from 3 to 15; which may be a monodentate ligand or a bidentate or greater ligand and is preferably a bidentate ligand, such as pyridine ligand, bipyridyl ligand, quinolinol ligand, hydroxyphenylazole ligand (e.g., hydroxyphenylbenzimidazole, hydroxyphenylbenzoxazole, hydroxyphenylimidazole)), an alkoxy ligand (preferably having a carbon number of 1 to 30, more preferably from 1 to 20, still more preferably from 1 to 10, such as methoxy, ethoxy, butoxy and 2-ethylhexyloxy), an aryloxy ligand (preferably having a carbon number of 6 to 30, more preferably from 6 to 20, still more preferably from 6 to 12, such as phenyloxy, 1-naphthyloxy, 2-naphthyloxy, 2,4,6-trimethylphenyloxy and 4-biphenyloxy), a heteroaryloxy ligand (preferably having a carbon number of 1 to 30, more preferably from 1 to 20, still more preferably from 1 to 12, such as pyridyloxy, pyrazyloxy, pyrimidyloxy and quinolyloxy), an alkylthio ligand (preferably having a carbon number of 1 to 30, more preferably from 1 to 20, still more preferably from 1 to 12, such as methylthio and ethylthio), an arylthio ligand (preferably having a carbon number of 6 to 30, more preferably from 6 to 20, still more preferably from 6 to 12, such as phenylthio), a hetero ring-substituted thio ligand (preferably having a carbon number of 1 to 30, more preferably from 1 to 20, still more preferably from 1 to 12, such as pyridylthio, 2-benzimizolylthio, 2-benzoxazolylthio and 2-benzothiazolylthio), or a siloxy ligand (preferably having a carbon number of 1 to 30, more preferably from 3 to 25, still more preferably from 6 to 20, such as triphenylsiloxy, triethoxysiloxy group and triisopropylsiloxy group), more preferably a nitrogen-containing heterocyclic ligand, an aryloxy ligand, a heteroaryloxy group or a siloxy ligand, still more preferably a nitrogen-containing heterocyclic ligand, an aryloxy ligand or a siloxy ligand.

The photoelectric conversion film 12 preferably has a p-type semiconductor layer and an n-type semiconductor layer, where at least one of the p-type semiconductor and the n-type semiconductor is an organic semiconductor and at the same time, a bulk heterojunction structure layer containing the p-type semiconductor and the n-type semiconductor is provided as an intermediate layer between those semiconductor layers. In such a case, by virtue of containing a bulk heterojunction structure in the photoelectric conversion film 12, the defect of the photoelectric conversion film 12 that the carrier diffusion length is short can be compensated and the photoelectric conversion efficiency can be enhanced. Incidentally, the bulk heterojunction structure is described in detail in Japanese Patent Application No. 2004-080639.

The photoelectric conversion film 12 preferably has a structure containing two or more repeating structures (tandem structures) of a pn-junction layer formed by a p-type semiconductor layer and an n-type semiconductor layer, and it is more preferred to insert an electrically conductive material thin layer between the repeating structures. The number of the repeating structures (tandem structures) of the pn-junction layer is not particularly limited but for increasing the photoelectric conversion efficiency, the number is preferably from 2 to 50, more preferably from 2 to 30, still more preferably from 2 or 10. The electrically conductive material is preferably silver or gold and most preferably silver. The tandem structure is described in detail in Japanese Patent Application No. 2004-079930.

The photoelectric conversion film 12 preferably contains a p-type semiconductor layer and an n-type semiconductor layer (preferably a mixed and dispersed (bulk heterojunction structure) layer)), where at least one of the p-type semiconductor and the n-type semiconductor contains an orientation-controlled organic compound, more preferably where both the p-type semiconductor and the n-type semiconductor contain an orientation-controlled (or controllable) organic compound. As for the organic compound, a compound having a π-conjugate electron is preferably used, and the π-electron plane is preferably aligned not perpendicularly to the substrate (electrode substrate) but at an angle close to parallel. The angle with respect to the substrate is preferably from 0 to 80°, more preferably from 0 to 60°, still more preferably from 0 to 40°, yet still more preferably from 0 to 20°, even yet still more preferably from 0 to 10°, and most preferably 0° (that is, in parallel to the substrate). As described above, the layer of the orientation-controlled organic compound is sufficient if it is contained even as a part of the entire photoelectric conversion film 12, but the ratio of the orientation-controlled portion to the entire photoelectric conversion film 12 is preferably 10% or more, more preferably 30% or more, still more preferably 50% or more, yet still more preferably 70% or more, even yet still more preferably 90% or more, and most preferably 100%. In such a state, by virtue of the controlled orientation of the organic compound contained in the photoelectric conversion film 12, the defect of the photoelectric conversion film 12 that the carrier diffusion length is short is compensated and the photoelectric conversion efficiency is enhanced.

In the case where the orientation of the organic compound is controlled, it is more preferred that the heterojunction plane (for example, the pn-junction plane) is not in parallel to the substrate. The heterojunction plane is preferably aligned not in parallel to the substrate (electrode substrate) but at an angle close to verticality as much as possible. The angle with respect to the substrate is preferably from 10 to 90°, more preferably from 30 to 90°, still more preferably from 50 to 90°, yet still more preferably from 70 to 90°, even yet still more preferably from 80 to 90°, and most preferably 90° (that is, perpendicular to the substrate). Such an organic compound layer with the heterojunction plane being controlled is sufficient if it is contained even as a part of the entire photoelectric conversion film 12. The ratio of the orientation-controlled portion to the entire photoelectric conversion film 12 is preferably 10% or more, more preferably 30% or more, still more preferably 50% or more, yet still more preferably 70% or more, even yet still more preferably 90% or more, and most preferably 100%. In such a case, the area of the heterojunction plane in the photoelectric conversion film 12 and in turn the amount of the carrier produced at the interface, such as electron, hole and electron-hole pair, can be increased and the photoelectric conversion efficiency can be enhanced. The photoelectric conversion efficiency can be enhanced particularly in the photoelectric conversion film where the alignments of both the heterojunction plane and the π-electron plane of the organic compound are controlled. These conditions are described in detail in Japanese Patent Application No. 2004-079931. The thickness of the organic dye layer is preferably larger in view of light absorption, but considering the proportion not contributing to the electric charge separation, the thickness of the organic dye layer is preferably from 30 to 300 nm, more preferably from 50 to 250 nm, still more preferably from 80 to 200 nm.

In the case of using a polymer compound as at least one of the p-type semiconductor (compound) and the n-type semiconductor (compound), the film is preferably formed by a wet film-forming method assured of easy production. In the case of using a dry film-forming method such as vapor deposition, a polymer may decompose and therefore, can be hardly used, but an oligomer may be preferably used instead. On the other hand, in the case of using a low molecular weight compound, a dry film-forming method is preferably employed, and a vacuum vapor deposition method is particularly preferred. In the vacuum vapor deposition method, basic parameters are, for example, the method of heating the compound, such as resistance heating vapor deposition or electron beam heating vapor deposition, the shape of the vapor deposition source, such as crucible or boat, the vacuum degree, the vapor deposition temperature, the substrate temperature, and the vapor deposition rate. In order to enable uniform vapor deposition, the vapor deposition is preferably performed while rotating the substrate. The vacuum degree is preferably higher, and the vacuum vapor deposition is performed at $10^{-4}$ Torr or less, preferably $10^{-6}$ Torr or less, more preferably $10^{-8}$ Torr or less. All steps at the vapor deposition are preferably performed in vacuum, and the compound is fundamentally prevented from coming into direct contact with oxygen in the outside air or with water. The above-described conditions in the vacuum vapor deposition affect the crystallinity, amorphous property, density, denseness and the like of the organic film and therefore, must be strictly controlled. The PI or PID control of the vapor deposition rate by using a quartz oscillator and a thickness monitor such as interferometer is preferably employed. In the case of simultaneously vapor-depositing two or more kinds of compounds, a co-vapor deposition method, a flash vapor deposition method or the like may be preferably used.

The subbing film 121 is provided, as described above, to suppress an increase of DC short or leak current due to irregularities on the lower electrode 11 surface.

The electron blocking film 122 is provided to reduce the dark current ascribable to injection of an electron from the lower electrode 11 and blocks the injection of an electron into the photoelectric conversion film 12 from the lower electrode 11. The electron blocking film 122 may be formed to serve also as the subbing film 121. For the electron blocking film, the above-described p-type semiconductor or hole-transporting organic compound may also be used.

The hole blocking film 124 is provided to reduce the dark current ascribable to injection of a hole from the upper electrode 13 and blocks injection of a hole into the photoelectric conversion film 12 from the upper electrode 13.

The hole blocking and buffer film 125 fulfills a function of reducing the damage given to the photoelectric conversion film 12 at the film formation of the upper electrode 13, as well as the function possessed by the hole blocking film 124. In the case of film-forming the upper electrode 13 as an upper layer of the photoelectric conversion film 12, a high energy particle present in the apparatus used for the film formation of the upper electrode 13, for example, in the case of sputtering, a sputter particle, a secondary electron, an Ar particle, an oxygen negative ion or the like, sometimes bombards the photoelectric conversion film 12 to cause deterioration of the photoelectric conversion film 12 and in turn degradation of the performance, such as increase of leak current or decrease of sensitivity. As one method for preventing such a problem, a buffer layer 125 is preferably provided as an upper layer of the photoelectric conversion film 12.

As for the material of the hole blocking and buffer film 125, an organic material such as copper phthalocyanine, PTCDA, acetylacetonate complex, BCP and Alq, an organic-metal compound, or an inorganic material such as MgAg and MgO is preferably used. Also, the hole blocking and buffer film 125 preferably has a high visible light transmittance so as not to inhibit the light absorption of the photoelectric conversion film 12, and it is preferred to select a material having no absorption in the visible region or use the film in a very small thickness. The appropriate thickness of the hole blocking and buffer film 125 varies, for example, depending on the construction of the photoelectric conversion film 12 or the film thickness of the upper electrode 13 but is preferably from 2 to 50 nm. For the hole blocking film, the above-described n-type semiconductor or electron-transporting organic compound may also be used.

The work function adjusting film 126 is provided to adjust the work function of the upper electrode 13 and thereby suppress the dark current. In the case where the upper electrode 13 is composed of a material having a relatively large work function (for example, 4.5 eV or more) (for example, any of ITO, IZO, $ZnO_2$, $SnO_2$, $TiO_2$ and FTO), a material containing a metal having a work function of 4.5 eV or less (for example, In) is used as the material of the work function adjusting film 126, whereby the dark current can be effectively suppressed. The advantage and the like in providing such a work function adjusting film 126 are described later.

The lower electrode 11 collects a hole by taking it out from the photoelectric conversion film 12 and therefore, is selected by taking into consideration the adhesion or electron affinity to an adjacent film, the ionization potential, the stability and the like. The upper electrode 13 ejects an electron by taking it out from the photoelectric conversion film 12 and therefore, is selected by taking into consideration the adhesion or electron affinity to an adjacent film, the ionization potential, the stability and the like.

In the production of the electrode, various methods are used according to the material. For example, in the case of ITO, the film is formed by a method such as electron beam method, sputtering, resistance heating vapor deposition, chemical reaction (e.g., sol-gel method), and coating of an indium tin oxide dispersion. In the case of ITO, a UV-ozone treatment, a plasma treatment or the like may be applied.

The conditions at the film formation of an electrode film which is transparent (transparent electrode film) are described below. The silicon substrate temperature at the film formation of the transparent electrode film is preferably 500° C. or less, more preferably 300° C. or less, still more preferably 200° C. or less, yet still more preferably 150° C. of less. Also, a gas may be introduced during the film formation of the transparent electrode film and the gas species is fundamentally not limited, but Ar, He, oxygen, nitrogen or the like may be used. A mixed gas of these gases may also be used. Particularly, in the case of an oxide material, an oxygen defect is formed in many cases and therefore, oxygen is preferably used.

The preferred range of the surface resistance of the transparent electrode film varies, for example, depending on whether the electrode is a lower electrode 11 or an upper electrode 13. In the case where the signal read-out part has a CMOS structure, the surface resistance of the transparent electrically conductive film is preferably 10,000 Ω/sq. or less, more preferably 1,000 Ω/sq. or less. In the case where the signal read-out part has a CCD structure, the surface resistance is preferably 1,000 Ω/sq. or less, more preferably 100 Ω/sq. or less. In use as the upper electrode 13, the surface resistance is preferably 1,000,000 Ω/sq. or less, more preferably 100,000 Ω/sq. or less.

The upper electrode 13 is preferably produced in a plasma-free state. When the upper electrode 13 is produced in a plasma-free state, the effect of the plasma on the substrate can be reduced and good photoelectric conversion properties can be obtained. Here, the plasma-free state means a state where plasma is not generated during the film formation of the upper electrode 13, or a state where the distance from a plasma generation source to the substrate is 2 cm or more, preferably 10 cm or more, more preferably 20 cm or more, and the plasma reaching the substrate is decreased.

Examples of the apparatus involving no generation of plasma during the film formation of the upper electrode 13 include an electron beam vapor deposition (EB vapor deposition) apparatus and a pulsed laser vapor deposition apparatus. As for such an EB vapor deposition apparatus or pulsed laser vapor deposition apparatus, apparatuses described, for example, Yutaka Sawada (supervisor), *Tomei Doden Maku no Shin Tenkai* (*New Development of Transparent Conductive Film*), CMC (1999), Yutaka Sawada (supervisor), *Tomei Doden Maku no Shin Tenkai II* (*New Development II of Transparent Conductive Film*), CMC (2002), *Tomei Doden Maku no Gijutsu* (*Technology of Transparent Conductive Film*), JSPS, Ohmsha (1999), and references cited therein may be used. In the following, the method of performing the film formation of the transparent electrode film by using an EB vapor deposition apparatus is referred to as an EB vapor deposition method, and the method of performing the film formation of the transparent electrode by using a pulsed laser vapor deposition apparatus is referred to as a pulsed laser vapor deposition method.

As regards the apparatus capable of realizing a state that the distance from a plasma generation source to the substrate is 2 cm or more and the plasma reaching the substrate is reduced (hereinafter referred to as a "plasma-free film-forming apparatus"), for example, an opposed-target sputtering apparatus or an arc plasma vapor deposition method may be considered, and apparatuses described, for example, in Yutaka Sawada (supervisor), *Tomei Doden Maku no Shin Tenkai* (*New Development of Transparent Conductive Film*), CMC (1999), Yutaka Sawada (supervisor), *Tomei Doden Maku no Shin Tenkai II* (*New Development II of Transparent Conductive Film*), CMC (2002), *Tomei Doden Maku no Gijutsu* (*Tech-* nology of Transparent Conductive Film), JSPS, Ohmsha (1999), and references cited therein may be used.

The material of the transparent electrode film is preferably a material which can be film-formed by a plasma-free film-forming apparatus, an EB vapor deposition apparatus or a pulsed laser vapor deposition apparatus, and suitable examples thereof include a metal, an alloy, a metal oxide, a metal nitride, a metal boride, an organic electrically conductive compound and a mixture thereof. Specific examples thereof include an electrically conductive metal oxide such as tin oxide, zinc oxide, indium oxide, indium zinc oxide (IZO), indium tin oxide (ITO) and indium tungsten oxide (IWO), a metal nitride such as titanium nitride, a metal such as gold, platinum, silver, chromium, nickel and aluminum, a mixture or laminate of such a metal and an electrically conductive metal oxide, an inorganic electrically conductive substance such as copper iodide and copper sulfide, an organic electrically conductive material such as polyaniline, polythiophene and polypyrrole, and a laminate thereof with ITO. Furthermore, those described in detail, for example in Yutaka Sawada (supervisor), *Tomei Doden Maku no Shin Tenkai* (*New Development of Transparent Conductive Film*), CMC (1999), Yutaka Sawada (supervisor), *Tomei Doden Maku no Shin Tenkai II* (*New Development II of Transparent Conductive Film*), CMC (2002), and *Tomei Doden Maku no Gijutsu* (*Technology of Transparent Conductive Film*), JSPS, Ohmsha (1999) may be also used.

The advantage in providing the work function adjusting film 126 is described below.

In the case of forming the upper electrode 13 from a material having high work function and high transparency, such as ITO, IZO, $ZnO_2$, $SnO_2$, $TiO_2$ and FTO, the dark current at the bias application to the upper electrode 13 becomes fairly large of about 10 $\mu A/cm^2$ when a voltage of 1 V is applied. One of causes of the dark current is considered to be a current flowing into the photoelectric conversion film 12 from the upper electrode 13 at the bias application. In the case where an electrode having high transparency, such as ITO, IZO, $ZnO_2$, $SnO_2$, $TiO_2$ and FTO, is used as the upper electrode 13, it is considered that the barrier when a hole moves to the photoelectric conversion film 12 becomes low due to the relatively large work function (4.5 eV or more) and injection of a hole into the photoelectric conversion film 12 readily occurs. In practice, when the work function of a metal oxide-based transparent electrode having high transparency, such as ITO, IZO, $SnO_2$, $TiO_2$ and FTO, is examined, for example, the work function of the ITO electrode is about 4.8 eV and is fairly high as compared with the work function of an Al (aluminum) electrode, which is about 4.3 eV. Also, metal oxide-based transparent electrodes other than ITO are known to have a relatively large work function of about 4.6 to 5.4, excluding AZO (Al-doped zinc oxide) of which work function is smallest and is about 4.5 eV (see, for example, FIG. 12 of *J. Vac. Sci. Technol.*, A17(4), July/August 1999, pp. 1765-1772).

In the case where the work function of the upper electrode 13 is relatively large (4.8 eV), it is considered that the barrier when a hole moves to the photoelectric conversion film 12 at the bias application becomes low and injection of a hole into the photoelectric conversion film 12 from the upper electrode 13 readily occurs, as a result, a large dark current is created. In this embodiment, a hole blocking film 124 is provided and therefore, the dark current is suppressed, but if the work function of the upper electrode 13 is large, even when a hole blocking film 124 is provided, it becomes difficult to suppress the dark current.

Accordingly, in this embodiment, a film for making the work function to be 4.5 eV or less is provided between the upper electrode 13 and the photoelectric conversion film 12.

Metals having a work function of 4.5 eV or less are listed below together with the properties thereof.

TABLE 1

Properties of Metals Having Small Work Function (excluding alkali metal)

| | Work Function (eV) | Melting Point (° C.) | Boiling Point (° C.) | Bulk Resistivity ($\Omega cm$) | Reaction with Air or Water |
|---|---|---|---|---|---|
| Ag | 4.2 | ○950 | ○2210 | ○$1.5 \times 10^{-6}$ | ○ inactive |
| Al | 4.3 | ○660 | ○2470 | ○$2.5 \times 10^{-6}$ | Δ oxide film |
| Ba | 2.5 | ○730 | ○1640 | Δ$4.6 \times 10^{-5}$ | X oxidized, soluble in water |
| Bi | 4.2 | ○270 | ○1610 | X$1.1 \times 10^{-4}$ | ○ inactive |
| Ca | 2.9 | ○840 | ○1480 | ○$3.2 \times 10^{-6}$ | X oxidized, soluble in water |
| Eu | 2.5 | ○820 | ○1600 | Δ$9.0 \times 10^{-5}$ | X oxidized, soluble in water |
| Ga | 2.6 | X28 | ○2400 | Δ$1.4 \times 10^{-5}$ | ○ inactive |
| Hf | 3.9 | ○2230 | Δ5200 | Δ$3.5 \times 10^{-5}$ | Δ oxide film |
| In | 4.1 | ○160 | ○2080 | ○$8.0 \times 10^{-6}$ | ○ inactive |
| La | 3.5 | ○920 | ○3460 | ○$5.7 \times 10^{-6}$ | X oxidized, soluble in water |
| Lu | 3.3 | ○1660 | ○3400 | Δ$7.9 \times 10^{-5}$ | X oxidized, soluble in water |
| Mg | 3.7 | ○650 | ○1090 | ○$3.9 \times 10^{-6}$ | X oxidized |
| Mn | 4.1 | ○1240 | ○1960 | X$2.6 \times 10^{-4}$ | X oxidized, soluble in water |
| Nb | 4.3 | ○2470 | Δ4740 | Δ$1.3 \times 10^{-5}$ | Δ oxide film |
| Nd | 3.2 | ○1020 | ○3070 | Δ$6.4 \times 10^{-5}$ | X soluble in water |
| Pb | 4.2 | ○330 | ○1740 | Δ$1.9 \times 10^{-5}$ | X oxidized |
| Sc | 3.5 | ○1540 | ○2830 | Δ$6.1 \times 10^{-5}$ | X oxidized, soluble in water |
| Sm | 2.7 | ○1080 | ○1790 | Δ$8.8 \times 10^{-5}$ | X soluble in water |
| Sn | 4.5 | ○230 | ○2270 | Δ$9.4 \times 10^{-5}$ | ○ inactive |
| Ta | 4.3 | ○3000 | Δ5430 | Δ$1.2 \times 10^{-5}$ | ○ inactive |
| Tb | 3.0 | ○1360 | ○3120 | | X oxidized, soluble in water |
| Th | 3.4 | ○1750 | Δ4790 | Δ$1.3 \times 10^{-5}$ | X powder ignition |
| Ti | 4.3 | ○1660 | ○3290 | Δ$5.8 \times 10^{-5}$ | ○ inactive |
| V | 4.3 | ○1890 | ○3377 | Δ$2.5 \times 10^{-5}$ | ○ inactive |
| W | 4.4 | ○3410 | Δ5660 | ○$4.9 \times 10^{-6}$ | ○ inactive |
| Y | 3.1 | ○1520 | Δ3340 | Δ$5.7 \times 10^{-5}$ | X oxidized |
| Zn | 4.3 | ○420 | Δ910 | ○$5.5 \times 10^{-6}$ | X oxidized |
| Zr | 4.1 | ○1850 | Δ4380 | Δ$4.0 \times 10^{-5}$ | Δ oxide film |

| | Material | Viewpoint |
|---|---|---|
| Preferred | Ag, Al, Ca, In, Mg | Resistance is small; melting point is not excessively low. |
| More preferred | Ag, In, Mg | Transparency is high. |
| Most Preferred | Ag, In | Reactivity is low. |

Third Embodiment of Photoelectric Conversion Element

In this embodiment, a construction of realizing a solid-state imaging device by using the photoelectric conversion element having a construction shown in FIG. 12B is described.

Figure 14:
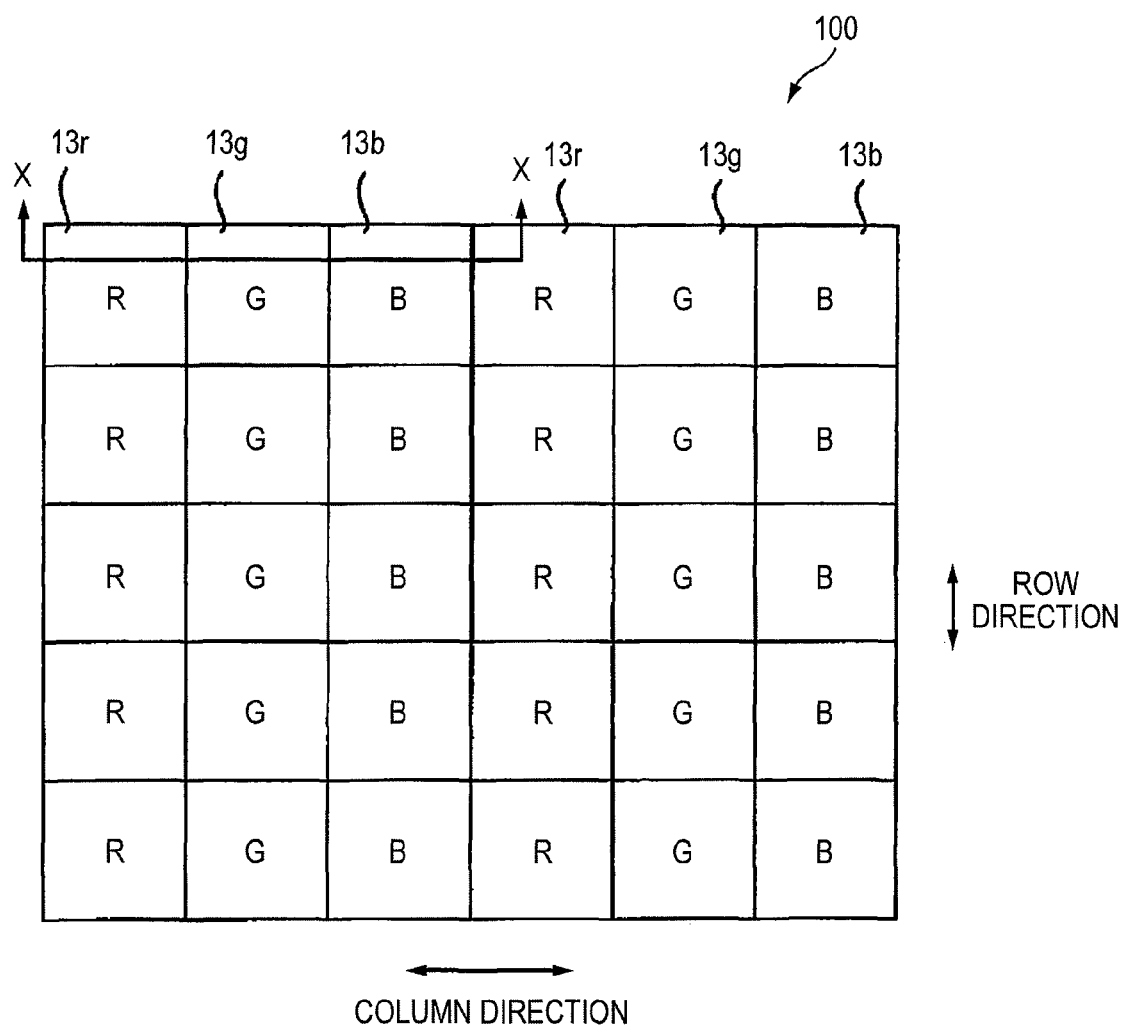
FIG. 14 is a partial surface schematic view of the imaging device for explaining the embodiment of the present invention.
Figure 15:
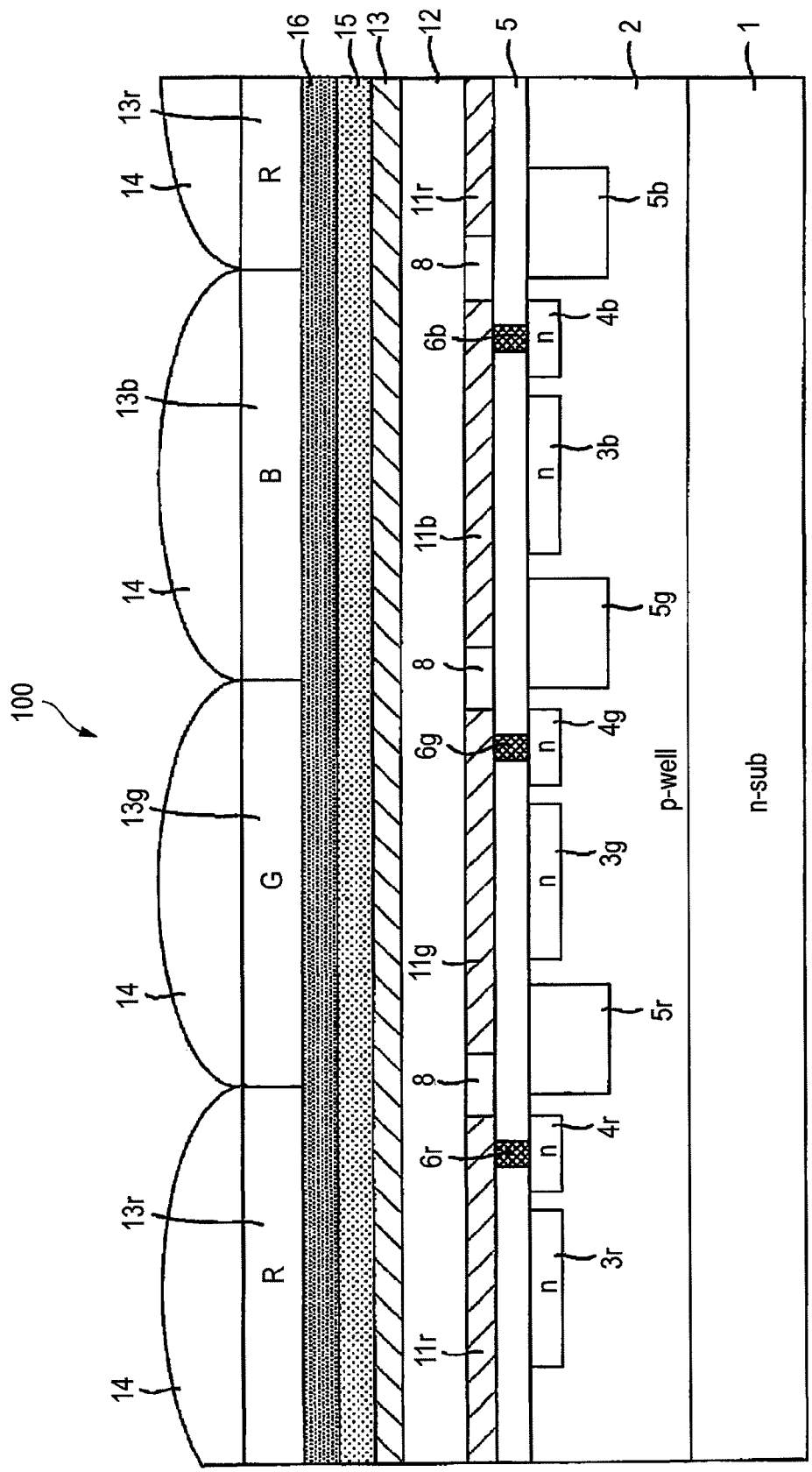
FIG. 15 is a cross-sectional schematic view cut along the A-A line of the imaging device shown in FIG. 14.

FIG. 14 is a partial surface schematic view of an imaging device for explaining the embodiment of the present invention, and FIG. 15 is a cross-sectional schematic view cut along the A-A line of the imaging device shown in FIG. 14. In FIG. 14, illustration of a microlens 14 is omitted. Also, in FIG. 15, the same constituents as those in FIG. 11 are denoted by like reference numerals.

A p-well layer 2 is formed on an n-type silicon substrate 1. In the following, the n-type silicon substrate 1 and the p-well layer 2 are collectively referred to as a semiconductor substrate. In the row direction and the column direction crossing with the row direction at right angles on the same plane above the semiconductor substrate, three kinds of color filters, that is, a color filter 13r mainly transmitting R light, a color filter 13g mainly transmitting G light, and a color filter 13b mainly transmitting B light, each is numerously arrayed.

As for the color filter 13r, a known material may be used and such a material transmits a part of infrared light in addition to R light. As for the color filter 13g, a known material may be used and such a material transmits a part of infrared light in addition to G light. As for the color filter 13b, a known material may be used and such a material transmits a part of infrared light in addition to B light.

For arraying the color filters 13r, 13g and 13b, a color filter array used in known single-plate solid-state imaging devices (e.g., Bayer array, longitudinal stripe, lateral stripe) may be employed.

Inside of the p-well layer 2 on the lower side of the color filter 13r, an n-type impurity region (hereinafter referred to as an "n region") 3r is formed to correspond to the color filter 13r, and an R photoelectric conversion element (which comes under the photoelectric conversion part C of FIG. 12B) corresponding to the color filter 13r is constructed by the pn junction of the n region 3r and the p-well layer 2.

Inside of the p-well layer 2 on the lower side of the color filter 13g, an n region 3g is formed to correspond to the color filter 13g, and a G photoelectric conversion element (which comes under the photoelectric conversion part C of FIG. 12B) corresponding to the color filter 13g is constructed by the pn junction of the n region 3g and the p-well layer 2.

Inside of the p-well layer 2 on the lower side of the color filter 13b, an n region 3b is formed to correspond to the color filter 13b, and a B photoelectric conversion element (which comes under the photoelectric conversion part C of FIG. 12B) corresponding to the color filter 13b is constructed by the pn junction of the n region 3b and the p-well layer 2.

A transparent electrode 11r is formed on the upper side of the n region 3r, a transparent electrode 11g is formed on the upper side of the n region 3g, and a transparent electrode 11b is formed on the upper side of the n region 3b. The transparent electrodes 11r, 11g and 11b are divided to correspond to the color filters 13r, 13g and 13b, respectively. The transparent electrodes 11r, 11g and 11b each has the same function as the lower electrode 11 of FIG. 11.

A photoelectric conversion film 12 in one-sheet construction shared in common among the color filters 13r, 13g and 13b is formed on the transparent electrodes 11r, 11g and 11b.

An upper electrode 13 in one-sheet construction shared in common among the color filters 13r, 13g and 13b is formed on the photoelectric conversion film 12.

A photoelectric conversion element (which comes under the photoelectric conversion part A of FIG. 12B) corresponding to the color filter 13r is formed by the transparent electrode 11r, the upper electrode 13 facing it, and a part of the photoelectric conversion film 12 sandwiched therebetween. This photoelectric conversion element is hereinafter referred to as an on-substrate R photoelectric conversion element, because it is formed on a semiconductor substrate.

A photoelectric conversion element (which comes under the photoelectric conversion part A of FIG. 12B) corresponding to the color filter 13g is formed by the transparent electrode 11g, the upper electrode 13 facing it, and a part of the photoelectric conversion film 12 sandwiched therebetween. This photoelectric conversion element is hereinafter referred to as an on-substrate G photoelectric conversion element.

A photoelectric conversion element (which comes under the photoelectric conversion part A of FIG. 12B) corresponding to the color filter 13b is formed by the transparent electrode 11b, the upper electrode 13 facing it, and a part of the photoelectric conversion film 12 sandwiched therebetween. This photoelectric conversion element is hereinafter referred to as an on-substrate B photoelectric conversion element.

A high-concentration n-type impurity region (hereinafter referred to as an "n+ region") 4r for accumulating an electric charge generated in the photoelectric conversion film 12 of the on-substrate R photoelectric conversion element is formed next to the n region 3r inside of the p-well layer 2. Incidentally, a light-shielding film is preferably provided on the n+ region 4r for preventing light from entering the n+ region 4r.

An n+ region 4g for accumulating an electric charge generated in the photoelectric conversion film 12 of the on-substrate G photoelectric conversion element is formed next to the n region 3g inside of the p-well layer 2. Incidentally, a light-shielding film is preferably provided on the n+ region 4g for preventing light from entering the n+ region 4g.

An n+ region 4b for accumulating an electric charge generated in the photoelectric conversion film 12 of the on-substrate B photoelectric conversion element is formed next to the n region 3b inside of the p-well layer 2. Incidentally, a light-shielding film is preferably provided on the n+ region 4b for preventing light from entering the n+ region 4b.

A contact part 6r comprising a metal such as aluminum is formed on the n+ region 4r, the transparent electrode 11r is formed on the contact part 6r, and the n+ region 4r and the transparent electrode 11r are electrically connected by the contact part 6r. The contact part 6r is embedded in an insulating layer 5 transparent to visible light and infrared light.

A contact part 6g comprising a metal such as aluminum is formed on the n+ region 4g, the transparent electrode 11g is formed on the contact part 6g, and the n+ region 4g and the transparent electrode 11g are electrically connected by the contact part 6g. The contact part 6g is embedded in the insulating layer 5.

A contact part 6b comprising a metal such as aluminum is formed on the n+ region 4b, the transparent electrode 11b is formed on the contact part 6b, and the n+ region 4b and the transparent electrode 11b are electrically connected by the contact part 6b. The contact part 6b is embedded in the insulating layer 5.

Inside of the p-well layer 2 other than the regions where the n regions 3r, 3g and 3b and the n+ regions 4r, 4g and 4b are formed, a signal read-out part 5r for reading out each of a signal according to the electric charge generated in the R photoelectric conversion element and accumulated in the n region 3r and a signal according to the electric charge accumulated in the n+ region 4r, a signal read-out part 5g for reading out each of a signal according to the electric charge generated in the G photoelectric conversion element and accumulated in the n region 3g and a signal according to the electric charge accumulated in the n+ region 4g, and a signal read-out part 5b for reading out each of a signal according to the electric charge generated in the B photoelectric conversion element and accumulated in the n region 3b and a signal according to the electric charge accumulated in the n+ region 4b are formed. For each of the signal read-out parts 5r, 5g and 5b, a known construction using a CCD or MOS circuit may be employed. Incidentally, a light-shielding film is preferably provided on each of the signal read-out parts 5r, 5g and 5b for preventing light from entering the signal read-out parts 5r, 5g and 5b.

Figure 16:
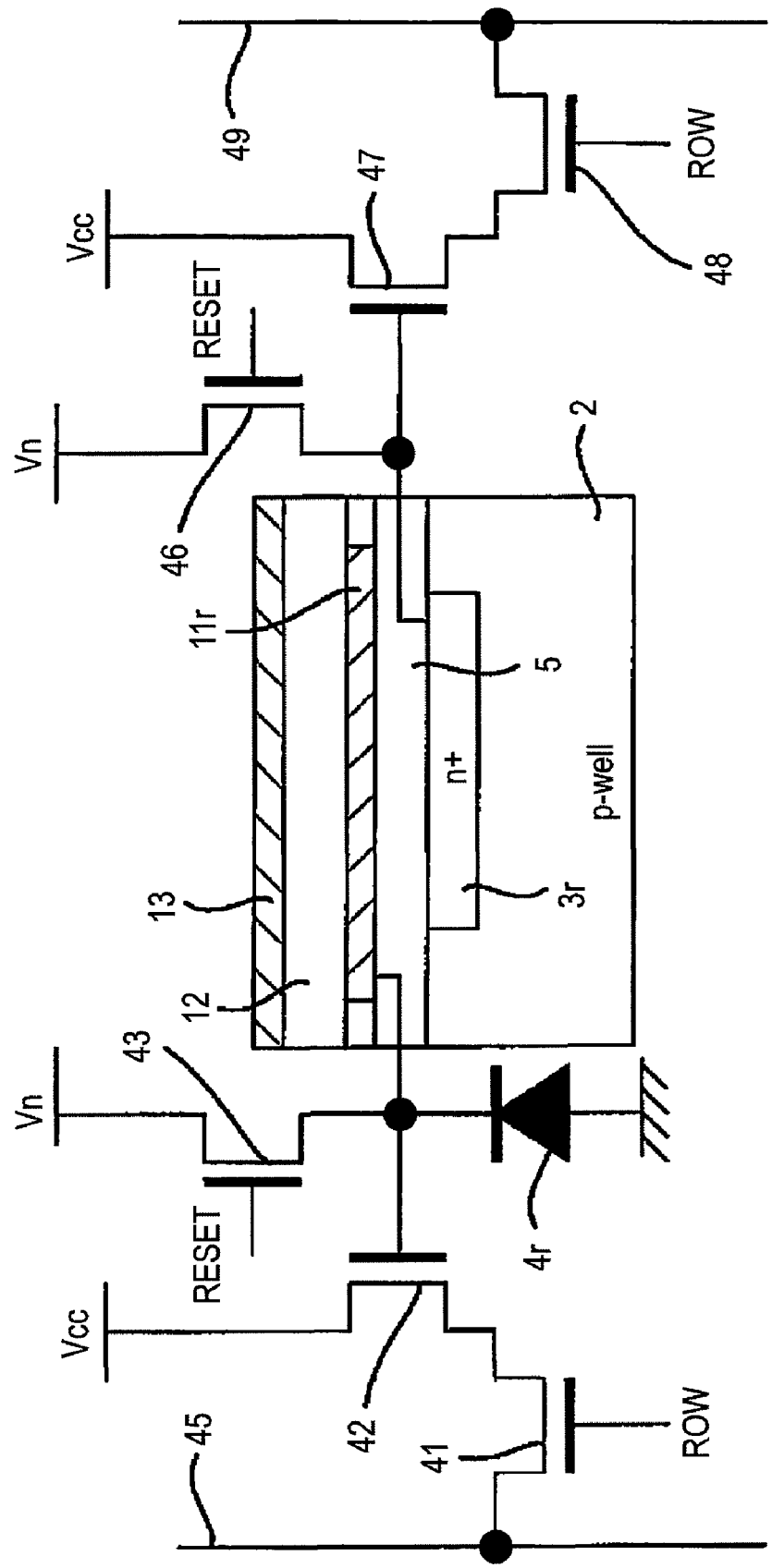
FIG. 16 is a view showing a specific construction example of the signal read-out part shown in FIG. 15.

FIG. 16 is a view showing a specific construction example of the signal read-out part 5r shown in FIG. 15. In FIG. 16, the same constituents as those in FIGS. 14 and 15 are denoted by like numerical references. Incidentally, the signal read-out parts 5r, 5g and 5b have the same construction and the description of the signal read-out parts 5g and 5b is omitted.

The signal read-out part 5r comprises a reset transistor 43 with a drain being connected to the n+ region 4r and a source being connected to a power source Vn, an output transistor 42 with a gate being connected to the drain of the reset transistor 43 and a source being connected to a power source Vcc, a row selection transistor 41 with a source being connected to the drain of the output transistor 42 and a drain being connected to a signal output line 45, a reset transistor 46 with a source being connected to the n region 3r and a source being connected to a power source Vn, an output transistor 47 with a gate being connected to the drain of the reset transistor 46 and a source being connected to a power source Vcc, and a row selection transistor 48 with a source being connected to the drain of the output transistor 47 and a drain being connected to a signal output line 49.

When a bias voltage is applied between the transparent electrode 11r and the upper electrode 13, an electric charge is generated according to light entered the photoelectric conversion film 12 and the electric charge moves to the n+ region 4r through the transparent electrode 11r. The electric charge accumulated in the n+ region 4r is converted by the output transistor 42 into a signal according to the electric charge amount. When the row selection transistor 41 is turned ON, the signal is output to the signal output line 45. After the output of the signal, the electric charge inside of the n+ region 4r is reset by the reset transistor 43.

The electric charge generated in the R photoelectric conversion element and accumulated in the n region 3r is converted by the output transistor 47 into a signal according to the electric charge amount. When the row selection transistor 48 is turned ON, the signal is output to the signal output line 49. After the output of the signal, the electric charge inside of the n region 3r is reset by the reset transistor 46.

In this way, the signal read-out part 5r can be constructed by a known MOS circuit comprising three transistors.

Backing to FIG. 15, protective layers 15 and 16 constituting a two-layer structure are formed on the photoelectric conversion film 12 for protecting the photoelectric conversion elements on the substrate. The color filters 13r, 13g and 13b are formed on the protective layer 16, and a microlens 14 is formed on each of the color filters 13r, 13g and 13b for condensing light on each of the corresponding n regions 3r, 3g and 3b.

This imaging device 100 is produced by forming the photoelectric conversion film 12 and then forming the color filters 13r, 13g and 13b, the microlens 14 and the like, but the formation of the color filters 13r, 13g and 13b or the microlens 14 involves a photolithography step and a baking step and in the case of using an organic material as the photoelectric conversion film 12, when the photolithography step or baking step is performed in the state of the photoelectric conversion film 12 being exposed, this causes deterioration in the properties of the photoelectric conversion film 12. In the imaging device 100, the protective films 15 and 16 are provided for preventing the properties of the photoelectric conversion film 12 from deterioration ascribable to such a production process.

The protective layer 15 is preferably an inorganic layer comprising an inorganic material and being formed by an ALCVD method. The ALCVD method is an atomic layer CVD method and enables the formation of a dense inorganic layer, and the layer formed can work out to an effective protective layer of the photoelectric conversion layer 9. The ALCVD method is also known as an ALE method or an ALD method. The inorganic layer formed by the ALCVD method preferably comprises $Al_2O_3$, $SiO_2$, $TiO_2$, $ZrO_2$, MgO, $HfO_2$ or $Ta_2O_5$, more preferably $Al_2O_3$ or $SiO_2$, and most preferably $Al_2O_3$.

The protective layer 16 is formed on the protective layer 15 for more enhancing the performance of protecting the photoelectric conversion film 12 and is preferably an organic layer comprising an organic polymer. The organic polymer is preferably parylene, more preferably parylene C. Incidentally, the protective layer 16 may be omitted, or the arrangement of the protective layer 15 and the protective layer 16 may be reversed. A high effect of protecting the photoelectric conversion film 12 is obtained particularly by the construction shown in FIG. 15.

In the imaging device 100 having the above-described construction, light in the infrared region from the light transmitted through the color filter 13r out of the incident light is absorbed in the photoelectric conversion film 12, and an electric charge according to the infrared light is generated there. Similarly, light in the infrared region from the light transmitted through the color filter 13g out of the incident light is absorbed in the photoelectric conversion film 12, and an electric charge according to the infrared light is generated there. Also, similarly, light in the infrared region from the light transmitted through the color filter 13b out of the incident light is absorbed in the photoelectric conversion film 12, and an electric charge according to the infrared light is generated there.

When a predetermined bias voltage is applied to the transparent electrode 11r and the upper electrode 13, the electric charge generated in the photoelectric conversion film 12 constituting the on-substrate R photoelectric conversion element moves to the n+ region 4r through the transparent electrode 11r and the contact part 6r and is accumulated there. A signal according to the electric charge accumulated in the n+ region 4r is read out by the signal read-out part 5r and output outside of the imaging device 100.

Similarly, when a predetermined bias voltage is applied to the transparent electrode 11g and the upper electrode 13, the electric charge generated in the photoelectric conversion film 12 constituting the on-substrate G photoelectric conversion element moves to the n+ region 4g through the transparent electrode 11g and the contact part 6g and is accumulated there. A signal according to the electric charge accumulated in the n+ region 4g is read out by the signal read-out part 5g and output outside of the imaging device 100.

Also, similarly, when a predetermined bias voltage is applied to the transparent electrode 11b and the upper electrode 13, the electric charge generated in the photoelectric conversion film 12 constituting the on-substrate B photoelectric conversion element moves to the n+ region 4b through the transparent electrode 11b and the contact part 6b and is accumulated there. A signal according to the electric charge accumulated in the n+ region 4b is read out by the signal read-out part 5b and output outside of the imaging device 100.

Furthermore, R light transmitted through the color filter 13r and transmitted through the photoelectric conversion film 12 enters the R photoelectric conversion element, and an electric charge according to the incident light quantity is accumulated in the n region 3r. Similarly, G light transmitted through the color filter 13g and transmitted through the photoelectric conversion film 12 enters the G photoelectric conversion element, and an electric charge according to the incident light quantity is accumulated in the n region 3g. Also, similarly, B light transmitted through the color filter 13b and transmitted through the photoelectric conversion film 12 enters the B photoelectric conversion element, and an electric charge according to the incident light quantity is accumulated in then region 3b. The electric charges accumulated in the n regions 3r, 3g and 3b are read out by the signal read-out parts 5r, 5g and 5b and output outside of the imaging device 100.

The array of signals read out and output from the n regions 3r, 3g and 3b becomes the same as the array of signals output from a single-plate color solid-state imaging device having a color filter array shown in FIG. 14 and therefore, by performing the signal processing used in a single-plate color solid-state imaging device, color image data where one pixel data have the data of R, G and B three color components can be produced. Also, infrared image data where one pixel data have the infrared color component data can be produced using the signals read out and output from the n+ regions 4r, 4g and 4b.

In this way, the imaging device 100 can output, to the exterior, the signal of R component according to the electric charge generated in the R photoelectric conversion element, the signal of G component according to the electric charge generated in the G photoelectric conversion element, the signal of B component according to the electric charge generated in the B photoelectric conversion element, the signal of IR component according to the electric charge generated in the photoelectric conversion element on the R substrate, the signal of IR component according to the electric charge generated in the photoelectric conversion element on the G substrate, and the signal of IR component according to the electric charge generated in the photoelectric conversion element on the B substrate. Therefore, when the imaging device 100 is used, two kinds of image data, that is, color image data and infrared image data, can be obtained by one imaging operation. Accordingly, this imaging device 100 can be utilized as an imaging device of an endoscope requiring an external image of an inspection-target site of a human body as well as an internal image of the site.

EXAMPLES

The present invention is described below by referring to Examples, but the present invention is of course not limited thereto.

Example 1

(Synthesis of Compound 1)

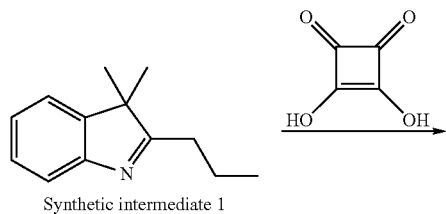

Synthetic intermediate 1

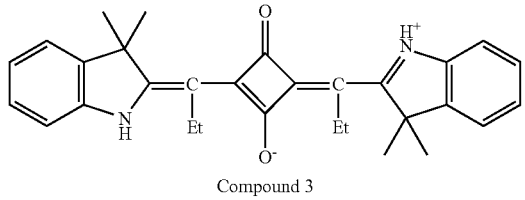

Compound 3

1-Butanol (15 mL) and 15 mL of toluene were added to 1.50 g of Synthetic Intermediate 1 synthesized by an ordinary method and 0.49 g of squaric acid, and the mixture was refluxed under heating for about 2 hours. After removing the toluene by distillation, the reaction solution was cooled to room temperature, and the precipitate was suction-filtered, washed with isopropanol and water in sequence, and dried to obtain a powder. This powder was boiled in isopropanol, then filtered, washed and dried to obtain Compound 1 (1.26 g, yield: 68%).

$^1$H NMR (CDCL$_3$, 300 MHz) δ=13.65 (br., 2H), 7.15-7.25 (m, 4H), 6.98-7.08 (m, 4H), 2.43 (s, 6H), 1.67 (s, 12H). MALDI-MS m/z 425 (MH+).

Synthesis of Synthetic Intermediate 2:

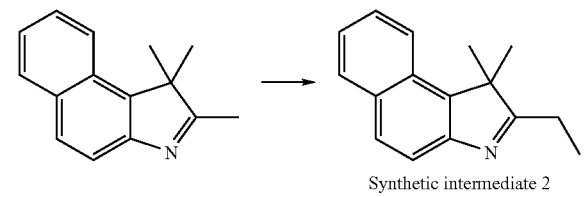

Synthetic intermediate 2

2,3,3-Trimethyl-4,5-benz-3H-indole (4.0 g) was dispersed in 30 ml of diethyl ether, and the dispersion was cooled using a dry ice-acetone bath. Thereto, 12.1 ml of a 1.58 mol/l n-butyllithium hexane solution was added and after stirring at room temperature for 1 hour, 4.12 g of iodomethane was further added. The resulting solution was left standing at room temperature overnight, and the obtained reaction solution was charged into water, adjusted to a pH of 10 or more by adding NaOH and then subjected to extraction by adding toluene. After concentrating the oil layer, the objective compound was separated and concentrated by silica gel column chromatography using an ethyl acetate-hexane mixed solution as the eluting solution, whereby Synthetic Intermediate 2 (3.86 g, yield: 91%) was obtained.

$^1$H, NMR (CDCL$_3$, 300 MHz) δ=8.01 (d, 1H), 7.96 (d, 1H), 7.85 (dd, 2H), 7.54 (t, 1H), 7.46 (t, 1H), 2.70 (q, 2H), 1.56 (s, 6H), 1.45 (t, 3H). MALDI-MS m/z 224 (MH+).

Example 2

(Synthesis of Compound 2)

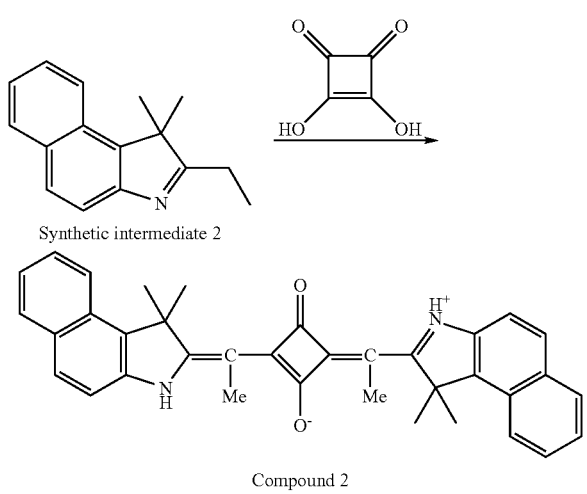

1-Butanol (10 mL) and 10 mL of toluene were added to 3.00 g of Synthetic Intermediate 2 and 0.82 g of squaric acid, and the mixture was refluxed under heating for about 6 hours. After removing the toluene by distillation, the reaction solution was cooled to room temperature, and the precipitate was suction-filtered, washed with isopropanol and water in sequence, and dried to obtain a powder. This powder was boiled in isopropanol, then filtered, washed and dried to obtain Compound 2 (0.86 g, yield: 24%).

$^1$H NMR (CDCL$_3$, 300 MHz) δ=13.70 (br., 2H), 7.96 (d, 2H), 7.88 (d, 2H), 7.79 (d, 2H), 7.53 (t, 2H), 7.35-7.46 (m, 4H), 2.54 (s, 6H), 1.96 (s, 12H). MALDI-MS m/z 525 (MH+).

Example 3

(Synthesis of Compound 3)

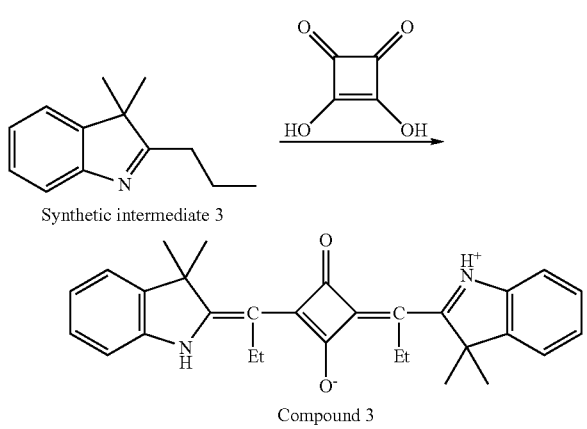

1-Butanol (10 mL) and 10 mL of toluene were added to 2.00 g of Synthetic Intermediate 3 synthesized by an ordinary method and 0.61 g of squaric acid, and the mixture was refluxed under heating for about 6 hours. After removing the toluene by distillation, the reaction solution was cooled to room temperature, and the precipitate was suction-filtered, washed with isopropanol and water in sequence, and dried to obtain a powder. This powder was boiled in isopropanol, then filtered, washed and dried to obtain Compound 3 (0.50 g, yield: 21%).

$^1$H NMR (CDCL$_3$, 300 MHz) δ=13.72 (br., 2H), 7.20-7.24 (m, 4H), 7.12 (d, 2H), 7.03 (t, 2H), 2.80 (br., 4H), 1.64 (s, 12H), 1.26 (t, 6H). MALDI-MS m/z 453 (MH+).

(Synthesis of Comparative Compound 1)

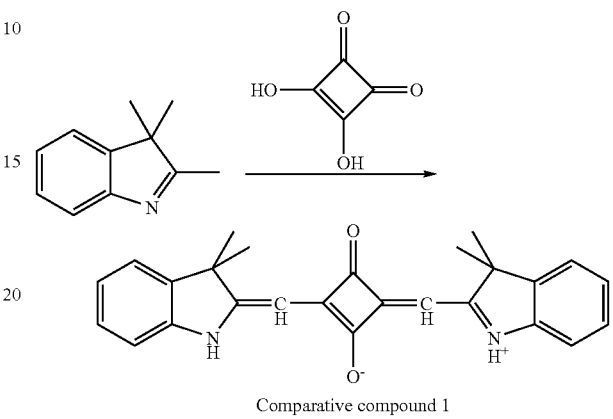

Comparative Compound 1 was synthesized according the literature (*Dyes and Pigments*, 39, 359-369 (1998)).

Synthesis of Comparative Compound 2:

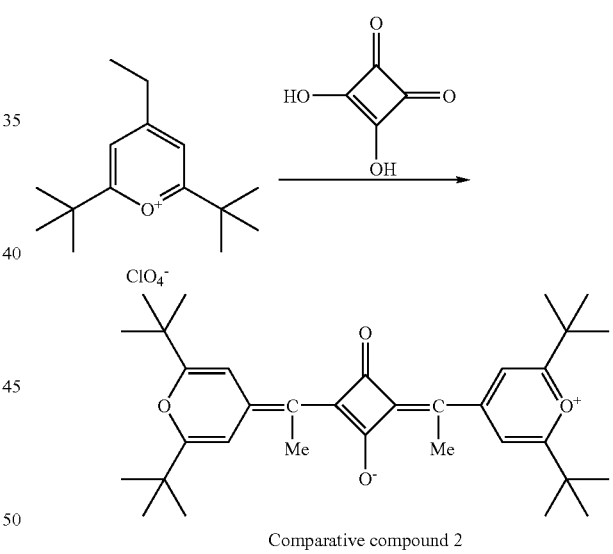

Comparative Compound 2 was synthesized according the literature (*Dyes and Pigments*, 46, 93-99 (2000)).

Example 4

About 1 mg of each of Compounds 1 to 3 and Comparative Compounds 1 and 2 was dissolved in 50 ml of chloroform, and the solution was further 10-fold diluted with chloroform to prepare a measurement solution. This solution was measured for the absorption spectrum by a spectrophotometer, UV-2400PC, manufactured by Shimadzu Corp. FIGS. 1 to 5 show the results obtained by normalization for the absorbance.

It is seen from FIGS. 1 to 5 that the compounds of the present invention and Comparative Compound 2 exhibit absorption in the near infrared region of 700 nm or more but Comparative Compound 1 exhibits absorption only in the visible region of 400 to 700 nm. The absorption maximum wavelengths are shown in Table 3.

Example 5

Each of Compounds 1 to 3 of the present invention and Comparative Compounds 1 and 2 was film-formed on a quartz substrate by vacuum heating vapor deposition. If decomposition of the compound occurs during the vapor deposition, the degree of vacuum changes for the worse. Whether decomposition took place or not in the vapor deposition process was judged based on the extent to which the degree of vacuum was worsened, and the results are shown in Table 2. Also, the decomposition initiating temperature of each sample was measured from the point at which the mass was decreased in TG-DTA, and shown in Table 2 together with the vapor deposition temperature and the difference between decomposition initiating temperature and vapor deposition temperature.

TABLE 2

| | Decomposition During Vapor Deposition | Decomposition Temperature of Compound by TG-DTA Measurement in $N_2$ (° C.) | Vapor Deposition Temperature of Compound (° C.) | Difference Between Decomposition Initiating Temperature and Vapor Deposition Temperature (° C.) |
|---|---|---|---|---|
| Compound 1 | none | 285 | 188 | 97 |
| Compound 2 | none | 294 | 232 | 62 |
| Compound 3 | none | 277 | 192 | 85 |
| Comparative Compound 1 | none | 171 | 241 | 70 |
| Comparative Compound 2 | occurred | 196 | 223 | 27 |

In Comparative Compound 2, decomposition involving worsening of the vacuum degree during vapor deposition was recognized. The decomposition is considered to occur because the difference between the decomposition initiating temperature and the vapor deposition temperature is only less than 30° C. In other compounds, decomposition during vapor deposition was not recognized and the difference between the decomposition temperature and the vapor deposition temperature was as large as 60° C., revealing good vapor deposition property involving no decomposition.

The absorption spectrum of each film-forming sample was measured by a spectrophotometer manufactured by Shimadzu Corp., and FIGS. 6 to 10 show the measurement results. Also, the thin-film absorption maximum wavelength (nm) and the maximum relative absorbance at 400 to 550 nm in the thin-film absorption are shown in Table 3 together with the solution absorption maximum wavelength (nm).

TABLE 3

| | Solution Absorption Maximum Wavelength (nm) | Thin-Film Absorption Maximum Wavelength (nm) | Maximum Relative Absorbance at 400 to 550 nm in Thin-Film Absorption |
|---|---|---|---|
| Compound 1 | 730 | 774 | 0.083 |
| Compound 2 | 762 | 806 | 0.083 |
| Compound 3 | 728 | 778 | 0.056 |
| Comparative Compound 1 | 654 | 699 | 0.152 |

TABLE 3-continued

| | Solution Absorption Maximum Wavelength (nm) | Thin-Film Absorption Maximum Wavelength (nm) | Maximum Relative Absorbance at 400 to 550 nm in Thin-Film Absorption |
|---|---|---|---|
| Comparative Compound 2 | 757 | 788 | 0.157 |

It is seen that the compounds of the present invention and Comparative Compound 2 exhibit large absorption in the near infrared region of 700 nm or more but Comparative Compound 1 has its main absorption in the visible region of 400 to 700 nm. Comparative Compound 2 exhibits absorption in the region of 400 to 550 nm that is not recognized in the solution absorption, and this is considered to be absorption of a decomposition product produced in the process of vapor deposition and result from contamination of the vapor-deposited film. The compounds of the present invention exhibit no such absorption derived from impurities and can be said to have good vapor deposition property. Consequently, it can be understood that the compounds of the present invention exhibit a high absorption intensity in the near infrared region of 700 nm or more and exhibit an absorption intensity of only 1/10 or less of the near infrared absorption at all wavelengths in 400 to 550 nm and a good near infrared absorbing organic thin film can be formed.

Example 6

Amorphous ITO of 30 nm was film-formed on a silicon substrate by sputtering to form a lower electrode, Compound A represented by the chemical formula shown below was film-formed to a thickness of 100 nm on the lower electrode by vacuum heating vapor deposition, and Compound 1 was film-formed to a thickness of about 50 nm by vacuum heating vapor deposition to form a photoelectric conversion film. Subsequently, Alq represented by the chemical formula shown below was film-formed to a thickness of about 50 nm on the film above by vacuum heating vapor deposition to form a hole blocking film, and amorphous ITO was film-formed to a thickness of 5 nm on the hole blocking film by sputtering to form an upper electrode, whereby Photoelectric Conversion Element 1 of Invention 1 was produced.

Inventions 2 to 4 and Comparative Examples 1 and 2

Elements were produced in the same manner except that Compound 1 was replaced by Compounds 2 to 4, Comparative Compound 3 (produced by Hayashibara Biochemical Laboratories, Inc.) or Comparative Compound 2 (synthesized according to *Dyes and Pigments,* 46, 93-99 (2000)), and designated as Inventions 2 to 4 and Comparative Examples 1 and 2.

In the above, the vacuum heating vapor depositions all were performed at a vacuum degree of $4 \times 10^{-4}$ Pa or less. The transmittance of the upper electrode itself in the wavelength region of 400 to 900 nm was 98% or more.

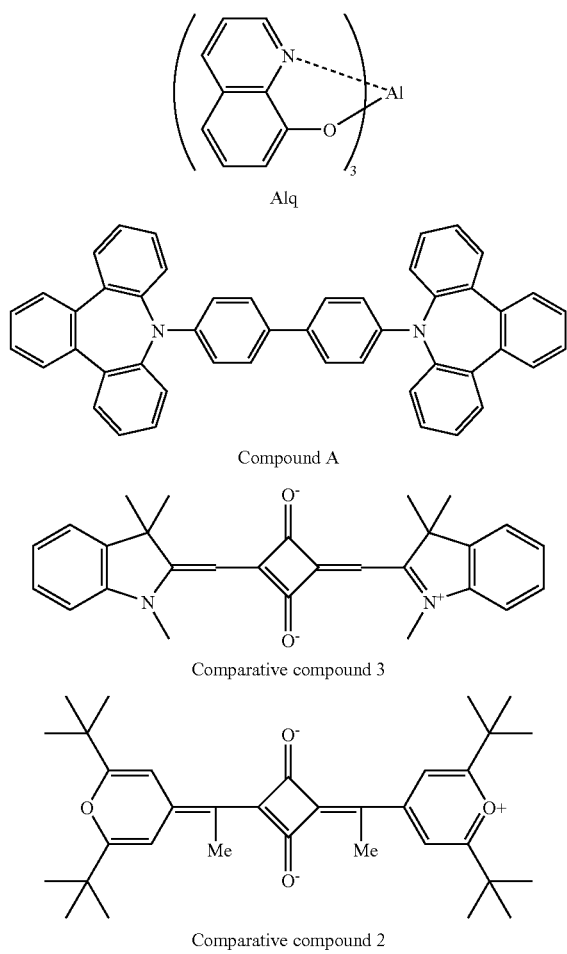

The elements obtained were measured for the absorption spectrum of the photoelectric conversion part, and the maximum absorption wavelength was recorded. As the maximum value of visible absorption based on the maximum absorption, the maximum absorbance in the region of 400 to 650 nm where the visibility is high, was recorded in terms of the relative value to the absorbance at the absorption maximum wavelength.

The absorption maximum wavelength of each of elements in Inventions 1 to 4 and Comparative Examples 1 and 2, the maximum value of visible absorption based on the maximum absorption, and the external quantum efficiency, in terms of the relative value, of photoelectric conversion when light at 720 nm and 800 nm was irradiated and a voltage was applied to the element, are shown in Table 4.

TABLE 4

| Compound | | Absorption Maximum Wavelength (nm) | Maximum Absorbance at 400 to 650 nm (relative value) | External Quantum Efficiency (relative value) | |
|---|---|---|---|---|---|
| | | | | 720 nm | 800 nm |
| Invention 1 | Compound 1 | 765 | 0.52 | 0.94 | 0.92 |
| Invention 2 | Compound 2 | 796 | 0.39 | 0.94 | 0.89 |
| Invention 3 | Compound 3 | 780 | 0.40 | 1.00 | 1.03 |
| Invention 4 | Compound 4 | 736 | 0.65 | 0.93 | 0.16 |
| Comparative Example 1 | Comparative Compound 3 | 680 | 0.82 | 0.33 | 0.00 |
| Comparative Example 2 | Comparative Compound 2 | 792 | 0.73 | 0.05 | 0.06 |

Visible absorption = 400 to 700 nm

As seen from the Table above, in Comparative Example 1, the maximum absorption wavelength is 700 nm or less and observed in the visible light region and the maximum absorbance at 400 to 650 nm is also disadvantageously large, whereas in Inventions 1 to 4 and Comparative Example 2, the maximum absorption wavelength is 700 nm or more and the maximum absorbance at 400 to 650 nm is relatively small, revealing that these elements have high light transparency and are assured of suitable properties as a visible light transmitting infrared-sensitive element. Furthermore, it is seen that in Comparative Examples 1 and 2, the external quantum efficiency at 720 nm and 800 nm which are the infrared light region is extremely low, whereas in Inventions 1 to 4, the external quantum efficiency of photoelectric conversion in the infrared region is high and these elements are useful as an infrared-sensitive element. In other words, it is understood that Inventions 1 to 4 can satisfy both high light transparency and high photoelectric conversion efficiency.

The present application claims foreign priority based on Japanese Patent Application (JP 2007-158568) filed Jun. 15 of 2007, the contents of which is incorporated herein by reference.

What is claimed is:

1. A photoelectric conversion element comprising:
a photoelectric conversion part consisting of a pair of electrodes and a photoelectric conversion film provided between the pair of electrodes,
wherein
the photoelectric conversion film consists of an organic photoelectric conversion material including a compound represented by formula (5):

Formula 5

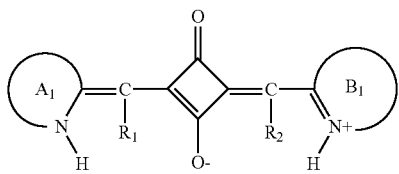

wherein A1 and B1 each independently represents a ring structure, and R1 and R2 each independently represents a substituent having a carbon number of 1 to 12; and wherein a thickness of the photoelectric conversion film is 30 nm to 300 nm.

2. The photoelectric conversion element as claimed in claim 1, wherein the formula (5) is represented by formula (6):

Formula (6)

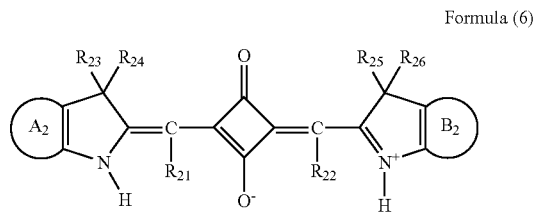

wherein R21 and R22 each independently represents a substituent having a carbon number of 1 to 12, R23 to R26 each independently represents a substituent, and A2 and B2 each independently represents a ring structure.

3. The photoelectric conversion element as claimed in claim 1,
wherein
the photoelectric conversion element has an absorption maximum wavelength of an absorption spectrum in a combined range of a visible region and an infrared region, the absorption maximum wavelength being 700 nm or more.

4. The photoelectric conversion element as claimed in claim 1,
wherein,
in the absorption spectrum of the photoelectric conversion element in a combined range of a visible region and an infrared region, the relative value of the maximum absorbance at 400 to 650 nm with respect to the absorbance at the maximum absorption wavelength is 0.9 or less.

5. The photoelectric conversion element as claimed in claim 1,
wherein
the photoelectric conversion element has sensitivity to light at 700 nm or more.

6. The photoelectric conversion element as claimed in claim 1,
wherein
the pair of electrodes comprises a transparent conducting oxide.

7. The photoelectric conversion element as claimed in claim 6,
wherein
the transparent conducting oxide is an indium tin oxide.

8. The photoelectric conversion element as claimed in claim 1, further comprising:
a semiconductor substrate on which the photoelectric conversion part is provided; and
at least one visible light photoelectric conversion part that is provided between the semiconductor substrate and the photoelectric conversion part, has an absorption maximum in the visible region of the absorption spectrum in the combined range of a visible region and an infrared region, and generates an electric charge according to light absorbed.

9. The photoelectric conversion element as claimed in claim 8,
wherein
the semiconductor substrate comprises:
an accumulation part that accumulates an electric charge generated in each of the photoelectric conversion part and the visible light photoelectric conversion part; and
a signal read-out part that reads out a signal according to the electric charge accumulated in the accumulation part.

10. The photoelectric conversion element as claimed in claim 1, further comprising:
a semiconductor substrate on which the photoelectric conversion part is disposed; and
at least one visible light photoelectric conversion part that is provided inside of the semiconductor substrate, has an absorption peak in the visible region of the absorption spectrum in the combined range of a visible region and an infrared region, and generates an electric charge according to light absorbed.

11. The photoelectric conversion element as claimed in claim 10,
wherein
the semiconductor substrate comprises:
an accumulation part that accumulates an electric charge generated in the photoelectric conversion part; and
a signal read-out part that reads out a signal according to the electric charge accumulated in the accumulation part.

12. The photoelectric conversion element as claimed in claim 8, which
comprises a plurality of visible light photoelectric conversion parts,
wherein
the visible light photoelectric conversion parts have an absorption peak at wavelengths different from each other.

13. The photoelectric conversion element as claimed in claim 12,
wherein
the visible light photoelectric conversion parts are stacked in the direction in which light is incident on the photoelectric conversion part.

14. The photoelectric conversion element as claimed in claim 12,
wherein
the visible light photoelectric conversion parts are arrayed in the direction vertical to the direction in which light is incident on the photoelectric conversion part.

15. The photoelectric conversion element as claimed in claim 12, which
comprise three visible light photoelectric conversion parts,
wherein
the three visible light photoelectric conversion parts comprise an R photoelectric conversion part that absorbs light in the red wavelength region, a G photoelectric conversion part that absorbs light in the green wavelength region, and a B photoelectric conversion part that absorbs light in the blue wavelength region.

16. The photoelectric conversion element as claimed in claim 8,
wherein
the photoelectric conversion part and the at least one visible light photoelectric conversion part are overlapped as viewed in plane such that light transmitted through the photoelectric conversion part enters the at least one visible light photoelectric conversion part.

17. The photoelectric conversion element as claimed in claim 1,
wherein
the photoelectric conversion film comprises at least one of a hole blocking layer and an electron blocking layer.

18. A solid-state imaging device comprising:
the photoelectric conversion element according to claim 6, wherein
two or more photoelectric conversion parts is disposed on the same plane in an array manner.

* * * * *